US012661248B2

(12) United States Patent
Nia

(10) Patent No.: US 12,661,248 B2
(45) **Date of Patent: *Jun. 23, 2026**

(54) RADIALLY SELF-EXPANDING STENTS

(71) Applicant: Edwards Lifesciences Corporation, Irvine, CA (US)

(72) Inventor: Nima V. Nia, Mission Viejo, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 914 days.

This patent is subject to a terminal disclaimer.

(21) Appl. No.: 17/850,116

(22) Filed: Jun. 27, 2022

(65) Prior Publication Data

US 2022/0323245 A1 Oct. 13, 2022

Related U.S. Application Data

(62) Division of application No. 16/686,673, filed on Nov. 18, 2019, now Pat. No. 11,559,415.

(Continued)

(51) Int. Cl.
*A61F 2/82* (2013.01)
*A61F 2/90* (2013.01)
(Continued)

(52) U.S. Cl.
CPC .................. *A61F 2/93* (2013.01); *A61F 2/90* (2013.01); *A61F 2/915* (2013.01); *A61F 2002/825* (2013.01)

(58) Field of Classification Search
CPC ................ A61F 2/82–2/945; A61F 2250/0082
See application file for complete search history.

(56) References Cited

U.S. PATENT DOCUMENTS 5,383,926 A 1/1995 Lock et al.
5,907,893 A 6/1999 Zadno-Azizi et al.
(Continued)

FOREIGN PATENT DOCUMENTS

FR 2788217 A1 7/2000
WO WO-2000041652 A1 7/2000
(Continued)

OTHER PUBLICATIONS

Cabrera M.S, et al., "Understanding the Requirements of Self-expandable Stents for Heart Valve Replacement: Radial Force, Hoop Force and Equilibrium," Journal of the Mechanical Behavior of Biomedical Materials, Elsevier, Amsterdam, Netherlands, Feb. 7, 2017, vol. 68, pp. 252-264.
(Continued)

*Primary Examiner* — Leslie A Lopez
(74) *Attorney, Agent, or Firm* — Chang and Hale LLP

(57) ABSTRACT

Described herein are radially self-expanding stents. The disclosed stents can be used to widen arteries and/or veins of a patient to counteract or combat narrowing of the arteries and/or veins associated with certain congenital diseases, such as aortic coarctation. As an example, the disclosed stents are configured to be placed at or near a narrowed portion of the aorta where the stent produces a radial outward force on the aorta. The radial force produced by the stent widens the aorta and causes the stent to expand with the aorta. The disclosed stents can be crimped to relatively small sizes for placement in small patients (e.g., less than about 10 kg in size) and can be configured to expand to widen the aorta and to accommodate growth in the patient.

5 Claims, 15 Drawing Sheets

Related U.S. Application Data

(60) Provisional application No. 62/823,901, filed on Mar. 26, 2019.

(51) Int. Cl.
   *A61F 2/915*        (2013.01)
   *A61F 2/93*         (2013.01)

(56) References Cited

U.S. PATENT DOCUMENTS

| | | | |
|---|---|---|---|
| 6,264,689 | B1 | 7/2001 | Colgan et al. |
| 6,579,314 | B1* | 6/2003 | Lombardi ............. A61L 31/048 |
| | | | 623/1.13 |
| 9,119,714 | B2 | 9/2015 | Shandas et al. |
| 9,314,335 | B2 | 4/2016 | Konno |
| 9,375,310 | B2 | 6/2016 | Chung et al. |
| 9,381,103 | B2 | 7/2016 | Abunassar |
| 10,702,407 | B1 | 7/2020 | Armer et al. |
| 12,004,939 | B1 | 6/2024 | Marshall et al. |
| 2006/0235509 | A1 | 10/2006 | Lafontaine |
| 2008/0004696 | A1 | 1/2008 | Vesely |
| 2008/0114452 | A1 | 5/2008 | Gabbay |
| 2008/0140179 | A1* | 6/2008 | Ladisa ................... A61F 2/915 |
| | | | 623/1.42 |
| 2009/0099644 | A1* | 4/2009 | Biadillah ................. A61F 2/91 |
| | | | 623/1.16 |
| 2011/0160763 | A1 | 6/2011 | Ferrera et al. |
| 2012/0158125 | A1 | 6/2012 | Obradovic |
| 2012/0330413 | A1 | 12/2012 | Pavcnik |
| 2014/0188221 | A1 | 7/2014 | Chung et al. |
| 2015/0127082 | A1* | 5/2015 | Sudhir .................. A61L 31/16 |
| | | | 623/1.11 |
| 2015/0366664 | A1 | 12/2015 | Guttenberg et al. |
| 2016/0008130 | A1 | 1/2016 | Hasin |
| 2016/0015538 | A1 | 1/2016 | Kariniemi et al. |
| 2016/0213499 | A1* | 7/2016 | Zheng ................... A61F 2/915 |
| 2016/0220361 | A1 | 8/2016 | Weber et al. |
| 2017/0000603 | A1 | 1/2017 | Conklin et al. |
| 2017/0000604 | A1 | 1/2017 | Conklin et al. |
| 2017/0014228 | A1 | 1/2017 | Emani et al. |
| 2017/0071732 | A1 | 3/2017 | Conklin et al. |
| 2018/0185144 | A1 | 7/2018 | Snyders |
| 2018/0289475 | A1 | 10/2018 | Chung et al. |
| 2019/0125517 | A1 | 5/2019 | Cully et al. |
| 2019/0209319 | A1 | 7/2019 | Konno |
| 2021/0353408 | A1 | 11/2021 | Chen et al. |
| 2022/0039945 | A1 | 2/2022 | Guttenberg et al. |
| 2023/0200986 | A1 | 6/2023 | Chung et al. |
| 2025/0161031 | A1 | 5/2025 | Jin et al. |

FOREIGN PATENT DOCUMENTS

| | | |
|---|---|---|
| WO | WO-2012018779 A2 | 2/2012 |
| WO | WO-2019175889 A1 | 9/2019 |
| WO | WO-2021061987 A1 | 4/2021 |

OTHER PUBLICATIONS

Forbes T.J., et al., "Intravascular Stent Therapy for Coarctation of the Aorta," Methodist DeBakey Cardiovascular Journal, ResearchGate, Berlin, Germany, Apr. 2014, vol. 10, No. 2, pp. 82-87.

Nia N.V., et al., "Can a Self-Expanding Pediatric Stent Expand with an Artery? Relationship of Stent design to Vascular Biology," Catheterization and Cardiovascular Interventions, Cardiovascular Systems, Inc., Wiley, Hoboken, NJ, 2021, vol. 98, Issue. 1, pp. 1-9, (10 Pages).

Stoeckel D., et al., "Self-Expanding Nitinol Stents—Material and Design Considerations," Nitinol Devices & Components, European Radiology, Dec. 1, 2003, pp. 1-12 (13 Pages), [Retrieved on Jan. 17, 2022] Retrieved from URL.

Tyagi S., et al., "Self-and Balloon-expandable Stent Implantation for Severe Native Coarctation of Aorta in Adults," American Heart Journal, Elsevier, Amsterdam, Netherlands, 2003, vol. 146, No. 5, pp. 920-928.

Stoeckel D., et al., "Self-expanding Nitinol Stents for the Treatment of Vascular Disease," Shape Memory Alloys for Biomedical Applications, Woodhead Publishing, 2009, pp. 237-256.

* cited by examiner

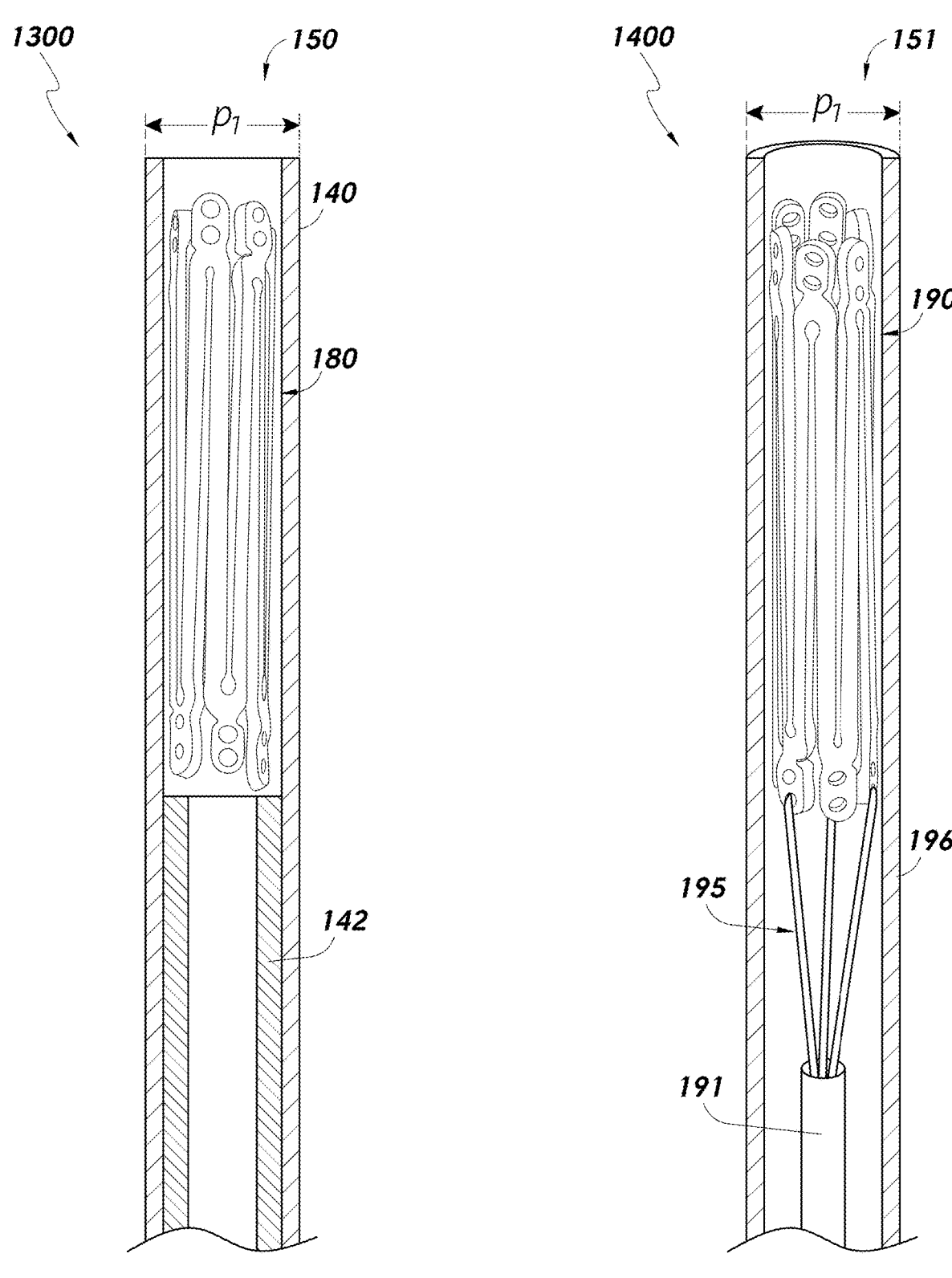
FIG. 13                    FIG. 14

*100*

PROVIDE RADIALLY SELF-EXPANDING STENT — *101*

COMPRESS STENT TO LOW-PROFILE CONFIGURATION — *102*

DISPOSE STENT IN DELIVERY SYSTEM — *103*

DELIVER, IN CRIMPED STATE, RADIALLY SELF-EXPANDING STENT — *104*

DEPLOY CRIMPED STENT AT OR NEAR LOCATION OF NARROWING OF VESSEL — *105*

RELEASE STENT TO ALLOW STENT TO SELF-EXPAND TO WIDEN VESSEL — *106*

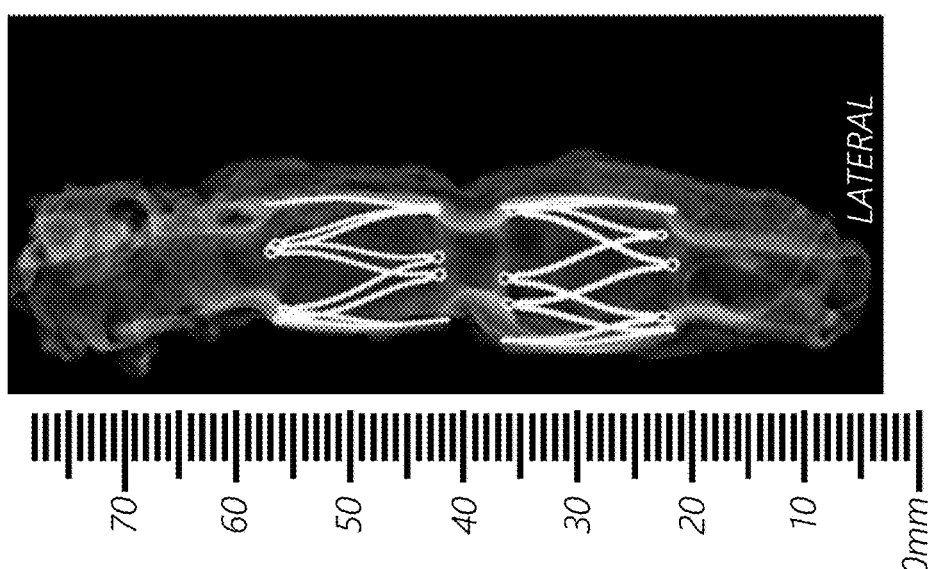
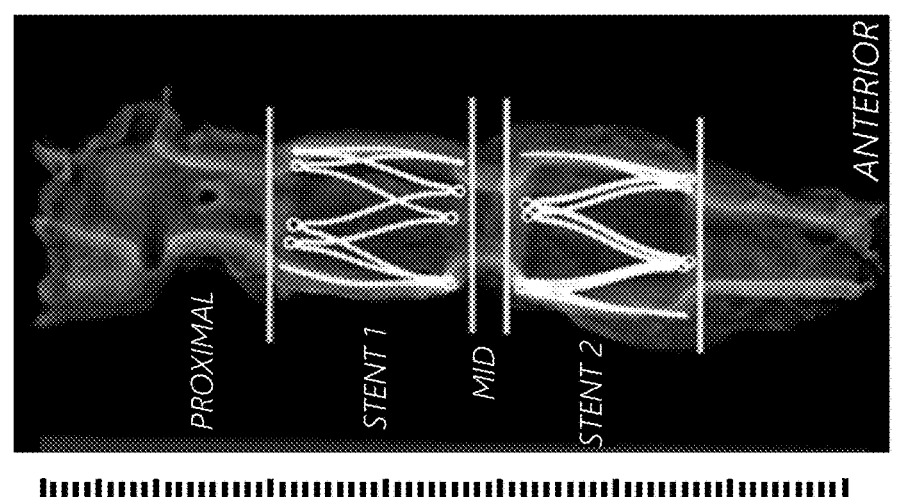
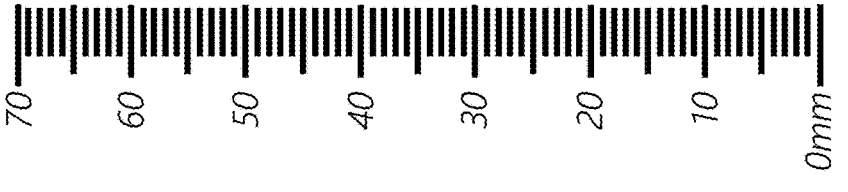
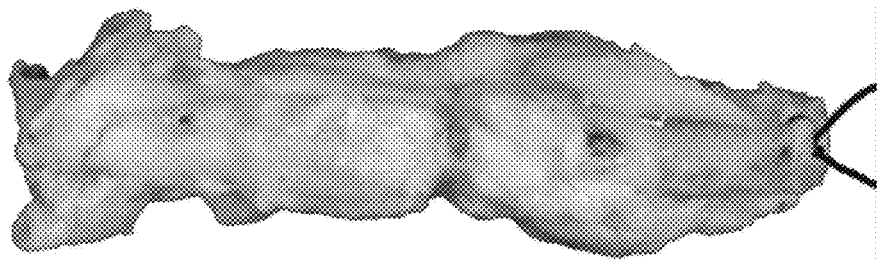
*FIG. 16A*

RADIALLY SELF-EXPANDING STENTS

RELATED APPLICATIONS

This application is a continuation of U.S. Utility patent application Ser. No. 16/686,673, filed Nov. 18, 2019 and entitled RADIALLY SELF-EXPANDING STENTS, which claims priority based on U.S. Provisional Patent Application Ser. No. 62/823,901, filed Mar. 26, 2019 and entitled RADI-ALLY SELF-EXPANDING STENTS, the complete disclo-sures of both of which are hereby incorporated by reference in their entireties.

BACKGROUND

Field

The present disclosure generally relates to stents.

Description of Related Art

Aortic coarctation is a congenital disease that relates to the narrowing or constriction of the aorta and affects many patients throughout the world, particularly children. This issue can lead to high blood pressure, exertional intolerance, can cause heart failure in infants and can cause high mor-bidity and mortality if untreated. Aortic coarctation can be treated using surgery, angioplasty, or stenting.

SUMMARY

In some implementations, the present disclosure relates to a radially self-expanding stent that includes a plurality of struts, individual struts having a wall thickness, and a plurality of joints configured to join alternating proximal and distal ends of adjacent struts of the plurality of struts. The stent is configured to produce an outward radial force with the stent having a diameter greater than or equal to a compact diameter and less than or equal to a fully expanded diameter, the outward radial force depending at least in part on the wall thickness of individual struts and configured to be sufficient to resist elastic recoil for aortic coarctation in a subject.

In some embodiments of the first aspect, individual struts have a curved shape. In some embodiments of the first aspect, adjacent struts are symmetric to each other.

In some embodiments of the first aspect, the wall thick-ness is configured so that the outward radial force is at least about 1 N. In further embodiments, the wall thickness is configured to that the outward radial force is less than or equal to about 5 N. In some embodiments of the first aspect, the wall thickness is at least 0.33 mm. In some embodiments of the first aspect, the wall thickness is at least 0.48 mm.

In some embodiments of the first aspect, the stent operates to produce a radially outward force with a diameter of at least about 8 mm. In some embodiments of the first aspect, the stent operates to produce a radially outward force with a diameter of at least about 14 mm. In some embodiments of the first aspect, the stent operates to expand a vessel from a diameter of about 8 mm to a diameter of about 14 mm.

In some embodiments of the first aspect, a height of the stent varies from the compact diameter to the fully expanded diameter so that the height is at least 14 mm at the fully expanded diameter and less than or equal to 20 mm at the compact diameter. The stent can be at least 25 mm in length in some embodiments and some configurations. In some embodiments of the first aspect, the compact diameter is less than or equal to about 2 mm. In some embodiments of the first aspect, the fully expanded diameter is greater than or equal to about 20 mm.

In some embodiments of the first aspect, individual struts form a repeating curved pattern. In further embodiments, individual struts are joined to adjacent struts at nodes between proximal and distal joints. In further embodiments, a height of the stent varies from the compact diameter to the fully expanded diameter so that the height is at least 20 mm at the fully expanded diameter and less than or equal to 42 mm at the compact diameter. In further embodiments, the wall thickness is configured so that the outward radial force is at least about 15 N. In further embodiments, the wall thickness is configured to that the outward radial force is less than or equal to about 20 N. In further embodiments, the wall thickness is at least 0.32 mm. For example, the outward radial force and/or wall thickness can advantageously be any amounts that are enough to keep the target vessel open without causing damage thereto.

In a second aspect, a method for treating aortic coarctation is provided. The method includes delivering a radially self-expanding stent in a crimped state. The method also includes deploying the radially self-expanding stent at a location of a narrowed vessel. The method also includes releasing the radially self-expanding stent such that the radially self-expanding stent produces a radially outward force that expands the narrowed vessel of a patient. The radially outward force is at least about 1 N when a diameter of the radially self-expanding stent is less than or equal to about 2 mm. In various embodiments, the outward radial force and/or wall thickness can advantageously be any amounts that are enough to keep the target vessel open without causing damage thereto.

In some embodiments of the second aspect, the radially outward force is at least about 5 N when a diameter of the radially self-expanding stent is less than or equal to about 20 mm. In some embodiments of the second aspect, the radially outward force is at least about 15 N when a diameter of the radially self-expanding stent is less than or equal to about 2 mm. In some embodiments of the second aspect, the radially outward force is at least about 20 N when a diameter of the radially self-expanding stent is less than or equal to about 20 mm. The numbers disclosed in this section relating to features of radially self-expanding stents are provided as examples only, and it should be understood that any other values that provide the desired results are applicable to embodiments of the present disclosure.

In some embodiments of the second aspect, the patient is a human child that weighs less than or equal to 10 kg. In some embodiments of the second aspect, the narrowed vessel expands from 8 mm to about 14 mm due at least in part to the radially outward force produced by the radially self-expanding stent.

In some embodiments of the second aspect, a diameter of the radially self-expanding stent varies from a compact diameter to a fully expanded diameter. In some embodi-ments of the second aspect, the compact diameter is less than or equal to about 2 mm. In some embodiments of the second aspect, the fully expanded diameter is at least 20 mm.

For purposes of summarizing the disclosure, certain aspects, advantages and novel features have been described herein. It is to be understood that not necessarily all such advantages may be achieved in accordance with any par-ticular embodiment. Thus, the disclosed embodiments may be carried out in a manner that achieves or optimizes one advantage or group of advantages as taught herein without necessarily achieving other advantages as may be taught or suggested herein.

BRIEF DESCRIPTION OF THE DRAWINGS

FIG. 13 shows a cross-sectional view of a delivery system for a radially self-expanding stent in accordance with one or more embodiments.

FIG. 14 shows a cross-sectional view of a delivery system for a radially self-expanding stent in accordance with one or more embodiments.

FIGS. 16A and 16B illustrate an example of stents being implanted in an abdominal artery of an animal for 90 days.

DETAILED DESCRIPTION OF SOME EMBODIMENTS

The headings provided herein are for convenience only and do not necessarily affect the scope or meaning of the claimed invention.

Overview

The following includes a general description of human cardiac anatomy that is relevant to certain inventive features and embodiments disclosed herein and is included to provide context for certain aspects of the present disclosure. In humans and other vertebrate animals, the heart generally comprises a muscular organ having four pumping chambers, wherein the flow of blood between the pumping chambers is at least partially controlled by various heart valves that are configured to open and close in response to a pressure gradient present during various stages of the cardiac cycle (e.g., relaxation and contraction) to at least partially control the flow of blood to respective regions of the heart and/or to associated blood vessels (e.g., pulmonary artery, aortic trunk, etc.).

Figure 1:
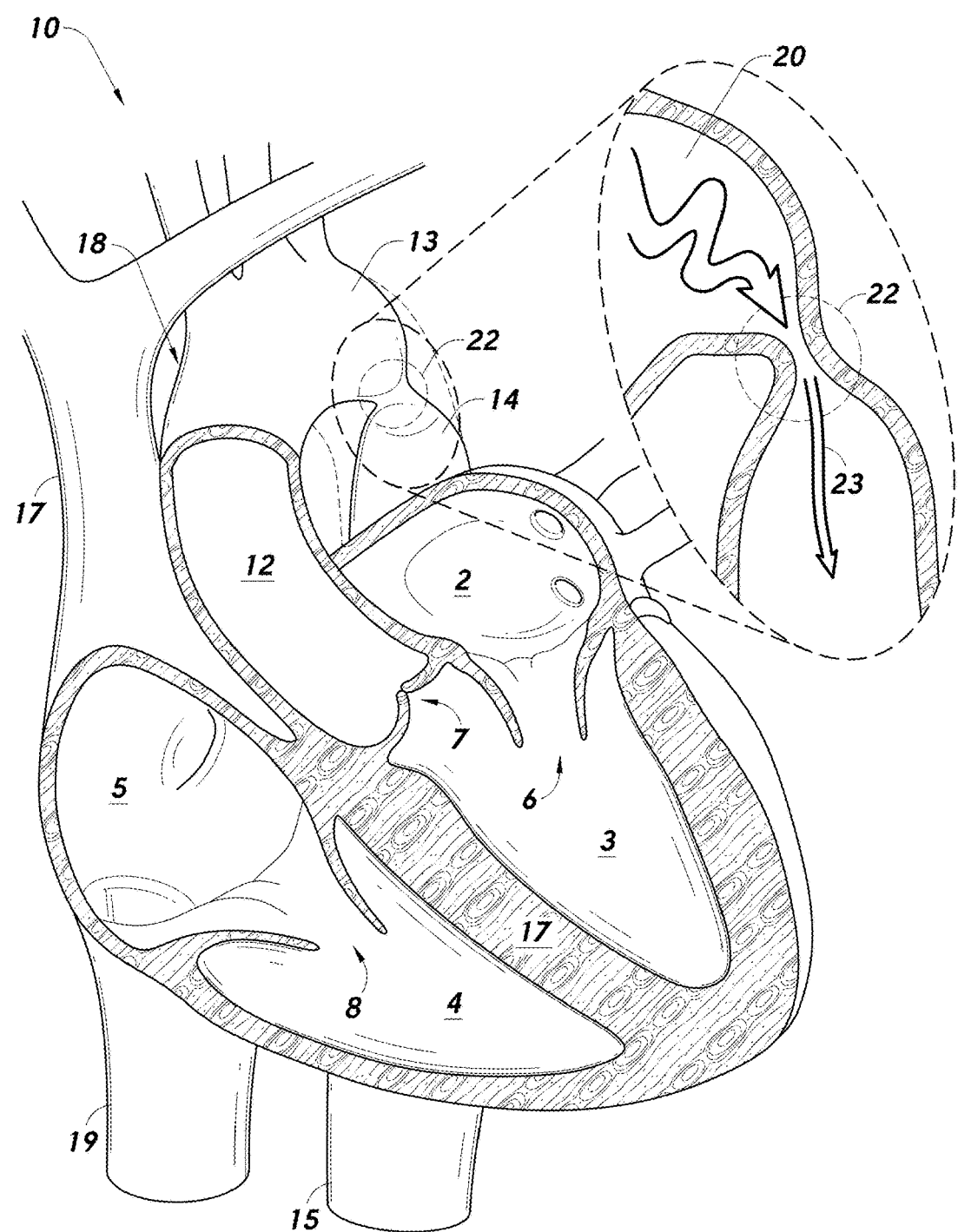
FIG. 1 illustrates a human heart with aortic coarctation.

FIG. 1 illustrates an example representation of a heart 1 having various features relevant to certain embodiments of the present inventive disclosure. Although certain embodiments are disclosed herein in the context of the anatomy of the heart, and particularly the aortic circulation and anatomy, it should be understood that radially self-expanding stent devices in accordance with embodiments and principles disclosed herein are relevant to any blood vessel or other conduit or lumen in which undesirable narrowing can be present.

With reference to FIG. 1, the four chamber of the heart 1 include the left atrium 2, the left ventricle 3, the right ventricle 4, and the right atrium 5. In terms of blood flow, blood generally flows from the right ventricle 4 into the pulmonary trunk (not shown) via the pulmonary valve (not shown). The pulmonary valve separates the right ventricle 4 from the pulmonary artery and is configured to open during systole so that blood may be pumped toward the lungs and close during diastole to prevent blood from leaking back into the heart from the pulmonary artery. The aorta 18 delivers oxygenated blood via circulation to the entire body from the left ventricle 3. With particular relevance to the present disclosure, the heart 1 further includes aortic anatomy 18, including the aortic valve 7, which provides an interface between the left ventricle 3 and the aortic anatomy 18 and controls the flow of oxygen-rich blood from the lungs to the body. The aortic valve 7 is configured to open during ventricular contraction (i.e., systole) to allow blood leaving the left ventricle 3 to enter the aorta 12, and close during ventricular expansion (i.e., diastole) to prevent blood from leaking back into the left ventricle 3. The aortic anatomy 18 further includes the ascending aorta 12 (i.e., aortic trunk), aortic arch 13, descending thoracic aorta 14, and abdominal aorta 15. One or more of the various portions/features of the above-recited aortic anatomy 18 may be referred to herein collectively as the "aorta," which term is used herein according to its broad and ordinary meaning.

With further reference to the heart diagram of FIG. 1, a wall of muscle 17, referred to as the septum, separates the left 2 and right 5 atria and the left 3 and right 4 ventricles. In addition to the pulmonary valve and the aortic valve 7, which are described above, the heart 1 includes two additional valves for aiding the circulation of blood therein, namely the tricuspid valve 8, and the mitral valve 6. The tricuspid valve 8 separates the right atrium 5 from the right ventricle 4. The tricuspid valve 8 generally has three cusps or leaflets and may generally close during systole and open during diastole. The mitral valve 6 generally has two cusps/leaflets and separates the left atrium 2 from the left ventricle 3. The mitral valve 6 is configured to open during diastole so that blood in the left atrium 2 can flow into the left ventricle 3, and close during diastole to prevent blood from leaking back into the left atrium 2.

The heart valves may generally comprise a relatively dense fibrous ring, referred to herein as the annulus, as well as a plurality of leaflets or cusps attached to the annulus. Generally, the size of the leaflets or cusps may be such that when the heart contracts the resulting increased blood pressure produced within the corresponding heart chamber forces the leaflets at least partially open to allow flow from the heart chamber. As the pressure in the heart chamber subsides, the pressure in the subsequent chamber or blood vessel may become dominant and press back against the leaflets. As a result, the leaflets/cusps come in apposition to each other, thereby closing the flow passage. The atrioventricular (i.e., mitral and tricuspid) heart valves may further comprise a collection of chordae tendineae and papillary muscles (not shown) for securing the leaflets of the respective valves to promote and/or facilitate proper coaptation of the valve leaflets and prevent prolapse thereof. The papillary muscles, for example, may generally comprise finger-like projections from the ventricle wall. The valve leaflets are connected to the papillary muscles by the chordae tendineae.

With further reference to the aortic anatomy 18 shown in FIG. 1, the ascending aorta 12 generally begins at the opening of the aortic valve 7 in the left ventricle 3 of the heart. The ascending aorta 12 can run through a common pericardial sheath with the pulmonary trunk. At the root of the ascending aorta 12, the blood vessel lumen may generally present three relatively small pockets (i.e., aortic sinuses, or "sinuses of Valsalva") between the cusps of the aortic valve 7 and the wall of the aorta. The left aortic sinus (not shown) contains the origin of the left coronary artery and the right aortic sinus (not shown) likewise gives rise to the right coronary artery. The posterior aortic sinus (not shown) does not give rise to a coronary artery.

The aortic arch 13 loops over the left pulmonary artery and the bifurcation of the pulmonary trunk, which are omitted from the diagram of FIG. 1 to allow for visibility of aspects of the aortic anatomy 18. The transition from the ascending aorta 12 to the aortic arch 13 may be considered to be at or near the pericardial reflection on the aorta. Between the aortic arch 13 and the pulmonary trunk is a network of autonomic nerve fibers, the cardiac plexus or aortic plexus. The left vagus nerve, which passes anterior to the aortic arch 13, gives off a major branch, the recurrent laryngeal nerve, which loops under the aortic arch just lateral to the ligamentum arteriosum. The aortic arch 13 has three major branches, including the brachiocephalic trunk, the left common carotid artery, and the left subclavian artery, which are shown in FIG. 1 but not called-out for simplicity. The brachiocephalic trunk supplies the right side of the head and neck as well as the right arm and chest wall, while the latter two together supply the left side of the same regions.

The aortic arch 13 transitions to the descending thoracic aorta 14 at or near the level of the intervertebral disc between the fourth and fifth thoracic vertebrae. The thoracic descending aorta 14 gives rise to the intercostal and subcostal arteries (not shown), as well as to the superior and inferior left bronchial arteries and variable branches to the esophagus, mediastinum, and pericardium (not shown). Its lowest pair of branches are the superior phrenic arteries, which supply the diaphragm, and the subcostal arteries for the twelfth rib. Therefore, the thoracic aorta 14 may be considered to run generally from the heart 1 to the diaphragm (not shown).

The abdominal aorta 15 generally begins at the aortic hiatus of the diaphragm at or near the level of the twelfth thoracic vertebra. The abdominal aorta 15 gives rise to lumbar and musculophrenic arteries, renal and middle suprarenal arteries, and/or visceral arteries (none of which are shown in FIG. 1 for simplicity). The abdominal aorta may be considered to extend down to the aortic bifurcation (not shown).

Aortic coarctation is a congenital heart defect involving a narrowing 22 of the aorta 18. Various types of aortic coarctation can occur in patients, including preductal coarctation, wherein the relevant narrowing is proximal to the ductus arteriosus, which is a blood vessel in developing fetuses that connects the trunk of the pulmonary artery to the proximal descending aorta 14 and/or aortic arch 13. Blood flow to the aorta 18 that is distal to the narrowing 22 is generally at least partially dependent on the ductus arteriosus, and therefore severe coarctation can be life-threatening. Pre-ductal coarctation can result when an intracardiac anomaly during fetal life decreases blood flow through the left side of the heart, leading to hypoplastic development of the aorta 18. In cases of ductal coarctation, the narrowing occurs at the insertion of the ductus arteriosus, wherein such narrowing can appear when the ductus arteriosus closes during fetal development. With respect to post-ductal coarctation, the undesirable narrowing is distal to the insertion of the ductus arteriosus. However, even with an open ductus arteriosus, blood flow to the lower body can be impaired by such narrowing. Post-ductal coarctation can be caused by the extension of the ductus arteriosus into the aorta during fetal life, wherein the contraction and fibrosis of the ductus arteriosus upon birth subsequently narrows the aortic lumen.

In addition to aortic coarctation, aortic stenosis is another form of aortic narrowing, which may be generally associated with undesirable narrowing in the aorta at or near the aortic root and/or valve 7. Although certain inventive devices and solutions are disclosed herein in the context of aortic coarctation, it should be understood that such devices/solutions are applicable to any other type of blood vessel narrowing, including aortic stenosis.

Treatments for correction of aortic coarctation can include surgery, angioplasty, and/or stenting. However, certain medical and non-medical issues can present in connection to such treatments. For example, surgical, angioplasty, and/or stenting-based treatments can be associated with one or more of the following complications, issues, and/or risks: risks associated with open heart surgery, reoccurrence of coarctation and stenosis, the lack of available pediatric stents, requirement of future replacement of a placed stent, stenosis, which can make further surgery likely or inevitable, aneurysm formation/development, and tears in one or more portions of the aorta. Stenting is generally the preferred form of treatment for aortic coarctation in patients that weigh over about 10 kg due at least in part to the efficacy of such solutions, the manageability, familiarity, and/or understandability of complications associated with such solutions, and cosmetic- and/or cost-related considerations. Issues associated with certain stenting solutions can include rupture, aneurysm, vascular injury, and re-dilation. Notably, there is a lack of stents available for patients that weigh less than about 10 kg (e.g., infants, babies, and toddlers). For example, due to tissue growth, deformation, and/or other environmental factors, stents implanted within the aorta or other blood vessel can become dislodged and/or migrate or shift from their desired target position, orientation, and/or location post-operatively over time due to growth of the implantation vessel.

To address the issues referenced above, as well as other potential issues, radially self-expanding stents that disclosed herein can advantageously open-up or widen the aorta 18 to counteract or combat narrowing of the aorta or other blood vessel of interest. Certain of the disclosed inventive stents are configured to be placed at or near a narrowed portion 22 of the aorta 18 (see FIG. 1), wherein the stent advantageously produces an outward radial force on the aorta 18. The radial force produced by the stent can serve to at least partially widen the aorta 18. In some implementations, stents in accordance with embodiments of the present disclosure are configured to continue to expand in accordance with the growth of the aorta 18. Furthermore, certain of the disclosed stents can be radially crimped/compressed to relatively small sizes/diameters for placement in anatomy of relatively small patients (e.g., less than about 10 kg in size) and can be configured to expand to widen the aorta 18 and to accommodate growth in the patient. Advantageously, this functionality can reduce the incidences of and/or need for lifestyle changes, emotional stress, uncertainties for families, additional surgical procedures, and/or health care costs.

Stent solutions in accordance with embodiments of the present disclosure can be configured to operate (e.g., to apply an outward radial force and/or to resist an inward radial force of the target vessel) between a relatively crimped or compact state and an expanded state. In some embodiments, the disclosed stents can have an initial crimped/compact delivery state and post-implantation expanded state, respectively, with respective diameters that are less than or equal to about 6 mm and/or greater than or equal to about 10 mm, less than or equal to about 4 mm and/or greater than or equal to about 15 mm, or less than or equal to about 2 mm and/or greater than or equal to about 20 mm. In some embodiments, the disclosed stents can operate with a height that ranges from between less than or equal to about 14 mm and/or greater than or equal to about 20 mm, less than or equal to about 10 mm and/or greater than or equal to about 25 mm, or less than or equal to about 20 mm and/or greater than or equal to about 42 mm. In a crimped state, the disclosed stents can be configured to be deliverable in a small delivery system (e.g., less than or equal to about 5-6 French). It should be understood that these numerical values are provided as examples only, and any other numbers producing the disclosed radial-expansion functionality would also fall within the scope of the present disclosure.

The disclosed stents can be configured to produce sufficient radial force to resist elastic recoil for coarctation and pulmonary artery and/or aortic stenosis. Stents in accordance with embodiments of the present disclosure can be configured so that when implanted in a patient, a patient's inflammatory response does not cause significant stenosis, restenosis, or aneurysm. Furthermore, the disclosed stents can be resistant to downstream embolization. The disclosed stents can be configured with nominal calibers suitable for the most common lesions (e.g., pulmonary artery stenosis and aortic coarctation). In some embodiments, the radial hoop strength of stents in accordance with embodiments of the present disclosure can be similar to balloon-expandable stents, such as the PALMAZ GENESIS® manufactured by CORDIS®, or the like. In certain implementations, the disclosed stents can be configured to be relatively conspicuous under applicable image-guidance modalities, such as magnetic resonance imaging, sonic/echo imaging, and/or the like. In some embodiments, the disclosed stents can be configured to provide relatively high radial force sufficient to overcome immediate recoil of the intended applications. Furthermore, embodiments of the present disclosure can advantageously provide "direct-stent" treatment techniques for native and/or iatrogenic lesions.

In some embodiments, stent devices in accordance with the present disclosure are configured to have/provide sufficient radial strength to withstand relevant structural loads, such as radial compressive forces imposed on the stent by the walls of a vessel as it supports such walls. Radial strength, which should be understood to refer to the ability of a stent to resist radial compressive forces, relates to a stent's radial yield strength and radial stiffness around a circumferential direction of the stent. The configuration of the struts, joints, and nodes can be tailored to achieve sufficient or targeted ranges of radial strength to widen a narrowed vessel and to maintain the widened vessel at a targeted size.

The sizes of the disclosed stents can be suitable for implantation in some human children, including children that are less than about 10 kg. The diameter of the aorta in a person typically decreases moving from the aortic sinus just above the aortic valve to the thoracoabdominal aorta at the level of the diaphragm. Typical diameters of aortas in children weighing about 12 kg can be about 14 mm at the aortic sinus and about 7 mm at the level of the diaphragm. Children weighing less than about 12 kg can have aortic diameters that are less than these numbers. The internal diameter of the aortic ostium can generally be linearly correlated with body length. Furthermore, studies have been conducted measuring aortic diameters for infants and children with results indicating the linear relationship between body length and aortic diameters, where an increase in body length from 30 cm to 140 cm corresponded to a linear change in the internal diameter of the aortic ostium of the ascending aorta from about 4.5 mm to about 19.5 mm and a linear change in the internal diameter of the aortic isthmus and of the descending aorta from about 3.5 mm to about 14.5 mm. Thus, the disclosed stents can advantageously be configured to function over a diameter range from about 2 mm to about 20 mm, allowing the disclosed stents to be used in patients that weigh less than or equal to about 10 kg.

It is to be understood that although certain stents described herein are described as being used to treat aortic coarctation, the disclosed stents can be used in a number of different applications. For example, the disclosed stents can be used to treat narrowing or constriction of other arteries and/or veins. As another example, the disclosed stents may be used as part of an artificial heart valve. In such implementations, two or more leaflets can be attached to the disclosed stents to form the heart valve, which can advantageously be configured to accommodate growth of the native valve orifice and/or annulus.

Radially Self-Expanding Stents

Figure 2A:
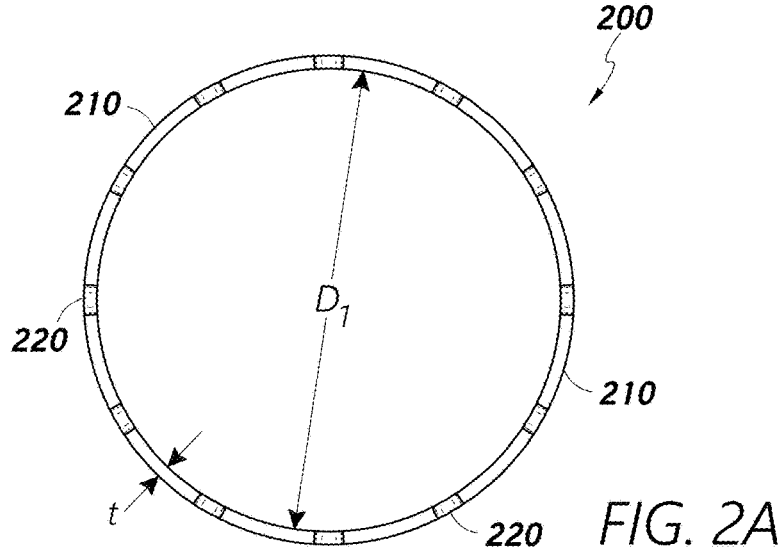
FIG. 2A illustrates an axial view of an example radially self-expanding stent in accordance with one or more embodiments.
Figure 2B:
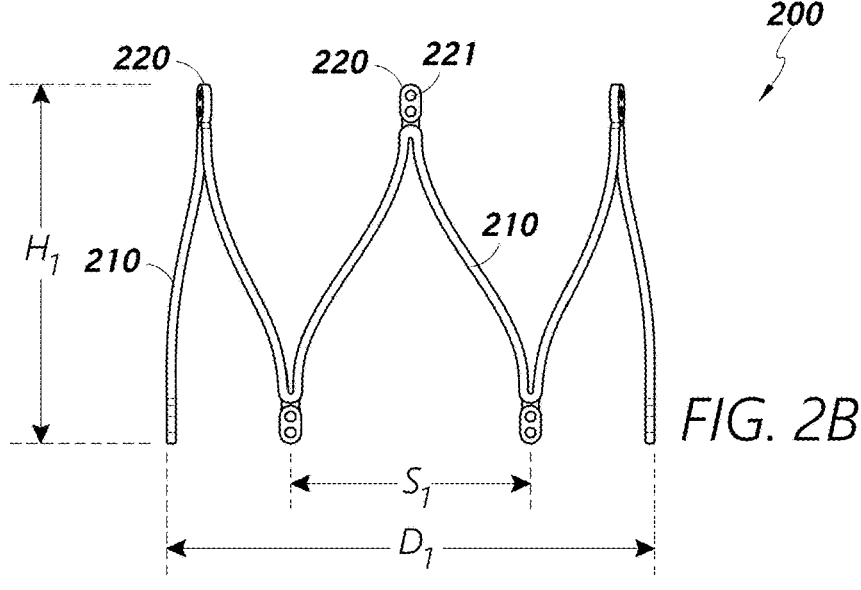
FIGS. 2B and 2C illustrate side views of an example radially self-expanding stent like that shown in FIG. 2A in accordance with one or more embodiments.
Figure 2C:
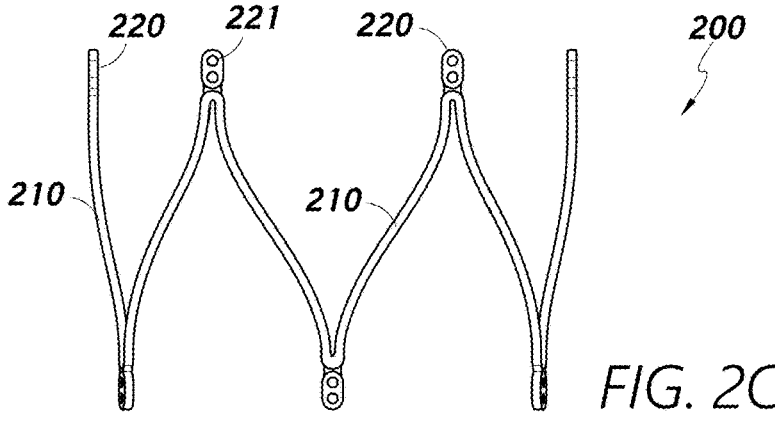
Figure 2D:
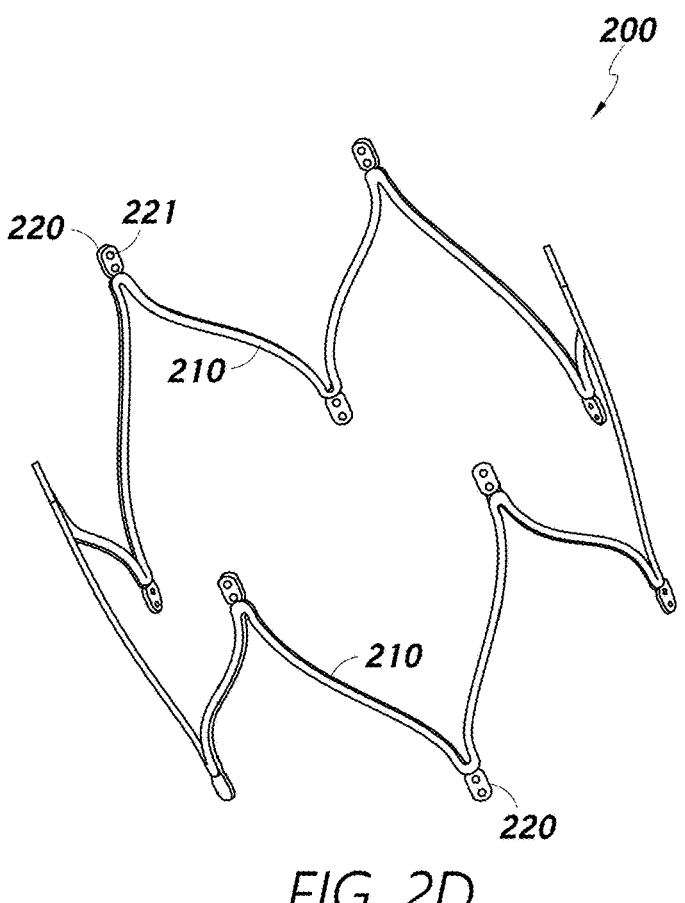
FIG. 2D shows a perspective view of an example radially self-expanding stent like that shown in FIGS. 2A-2C in accordance with one or more embodiments.
Figure 2E:
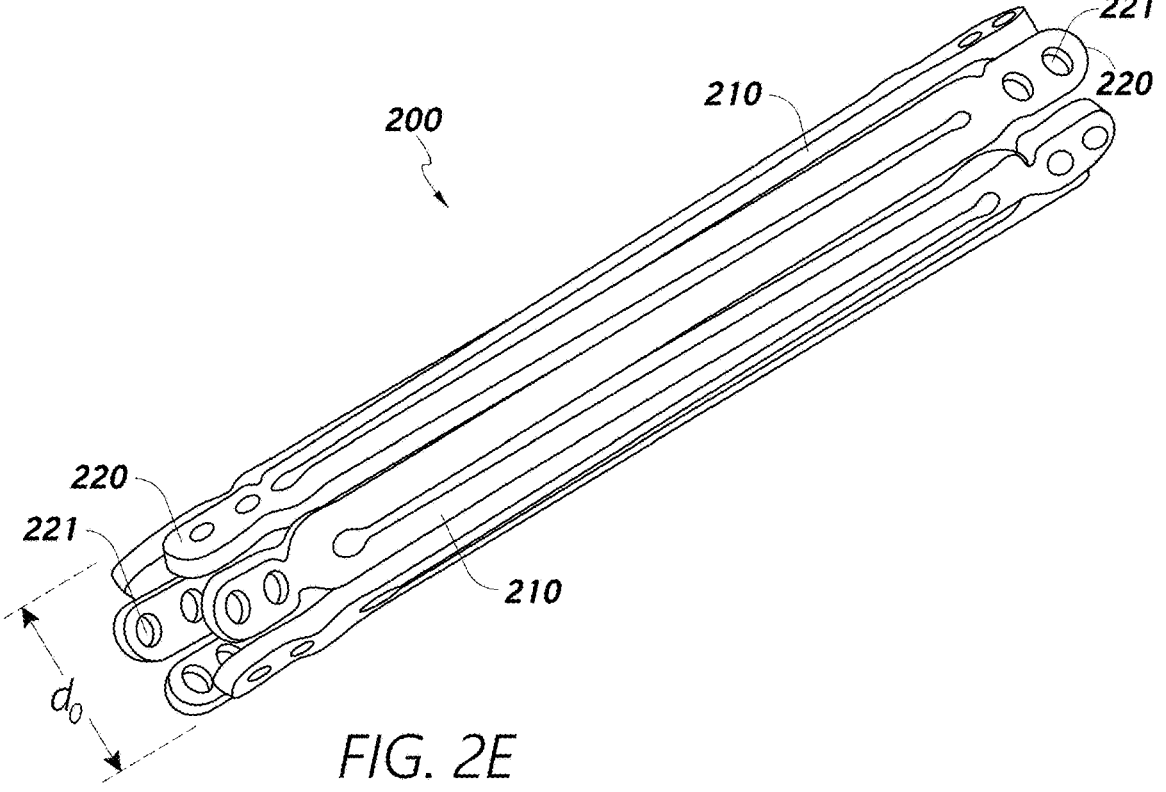
FIG. 2E shows a perspective view of an example radially self-expanding stent like that shown in FIGS. 2A-2D in a compressed configuration in accordance with one or more embodiments.

FIGS. 2A-2E illustrate an example of a radially self-expanding stent 200. In particular, FIGS. 2A-2D illustrate various axial, side, and perspective views, respectively, of the stent 200 in an initial expanded state, whereas FIG. 2E illustrates a perspective view of the stent 200 in a compact or crimped state. The stent 200 can generally form a tubular structure, as shown in the top view of FIG. 2A. The diameter $D_1$ of the stent 200 can vary from about 2 mm to about 20 mm between a crimped state and an initial expanded state prior to any growth that may occur post-operatively (i.e., "initial expanded state"). As shown in FIG. 2B, the height $H_1$ of the stent 200 can vary from about 14 mm to about 20 mm. Generally, an inverse relationship may exist between the height $H_1$ and the diameter $D_1$ and/or the strut spacing $S_1$ as the configuration of the stent 200 changes between a compressed/default state and the initial expanded state and/or vice versa. At each diameter D and corresponding height H, the stent 200 can produce a force pointing/directed radially outward from an axis of the stent to widen a conduit or vessel (e.g., an aorta). The radial outward force can further cause the stent 200 to radially expand or grow with expansion of the vessel in which it is implanted. In some implementations and embodiments, expansion of the stent 200 after implantation thereof can be caused at least in part by self-expanding characteristics of the stent 200 in connection with shape memory of the frame of the stent 200. For example, the stent 200 can comprise memory metal, such as Nitinol®, which is a nickel-titanium alloy. Such devices may have a memory shape such that the stent advantageously self-deploys relatively gently and/or atraumatically without the need for a deployment balloon to induce the desired expansion. Shape-memory stents in accordance with embodiments of the present disclosure can advantageously comprise super-elastic properties. Furthermore, in some embodiments, stents in accordance with the present disclosure can be at least partially configured to conform to the shape of the target vessel in which is it is deployed, such as to the aortic arch and/or descending aorta, which can be somewhat tortuous in some patients. The stent 200 can be deployed by retracting a delivery sheath/catheter to expose the stent in the target vessel, and/or by pushing the stent distally out of the delivery sheath/catheter.

The stent 200 can be configured to expand until it reaches the target vessel wall and exerts a continuous outward force onto the wall of the vessel, such that any remodeling by, or engagement with, the target vessel after implantation may be achieved/accommodated by the stent 200 through subsequent (e.g., post-operative) expansion thereof. Therefore, the expansion of the target portion of the target vessel and/or of the target vessel itself may be caused by the force applied by the stent 200 due to shape-memory characteristics thereof and/or growth of the patient in which the stent 200 is implanted. For example, Where the stent 200 is at least partially sutured to, embedded in, or otherwise attached/secured to the vessel wall, expansion of the wall due to patient growth may cause expansion of the stent.

The stent 200 may be tubular and/or annular but may also be provided in other shapes. In addition, the stent 200 can be adaptable or pliable such that the cross-sectional and/or axial shape thereof can conform to the shape of the vessel in which it is implanted. In other words, the shape of the stent 200 may depend at least in part on the cross-section shape of the vessel at the implant site.

The stent 200 is adapted to be radially crimped and radially expanded. In a crimped state, the stent 200 can be less than about 5 French. In the crimped state, the stent 200 can be navigated through narrow passages in the vasculature during positioning of the device, such as within a delivery system sheath/catheter. The stent 200 is configured to provide targeted outward radial forces as it transitions from the crimped state to an initial expanded state, and further to a post-operative expanded state. This facilitates adequate deployment at the final location because it can begin to provide outward radial forces upon implantation without requiring the stent 200 to first be radially expanded manually. The stent 200 is configured to provide operability at a range of sizes/diameters so that the stent 200 continues to provide targeted outward radial forces as the vessel expands and/or the patient grows.

The stent 200 includes a plurality of struts 210 joined by/at joints 220 at proximal and distal ends of the stent 200. With respect to the illustrated orientations of FIGS. 2B and 2C, either the top or bottom portion of the stent 200 may be the distal end or the proximal end of the stent 200 and/or associated delivery system. Each strut 210 is advantageously curved and is joined to an adjacent strut 210 at a corresponding joint 220. For example, the struts 210 can advantageously have an S-curve shape, which may provide characteristics that can be expanded/bent without causing substantial damage to the stent/joints. In some embodiments, the joints 220 alternate between proximal and distal ends of the stent 200, as shown. For example, a first strut 210 can be joined to a second strut 210 at a first joint 220 at a proximal end of the stent 200 and a second strut 210 is joined to a third strut 210 at a second joint 220 at a distal end of the stent 200. This pattern generally repeats to form the tubular structure of the stent 200. The joints 220 can be configured to allow the struts 210 to circumferentially expand and contract to produce radial expansion/contraction of the stent 200 and can contribute to the radial outward force produced by the stent 200.

In some embodiments, the struts 210 can be of the same shape with adjacent struts being vertical (e.g., running from proximal to distal) and/or circumferential reflections of each other. In certain implementations, the struts 210 can have a similar shape as a portion of the graph of the tangent function, or may have any other at least partially curved shape.

For applications relating to interventions for children and infants, who generally have relatively small anatomy (e.g., aortic diameter), it can be desirable or critical for dimensions and features of a stent for implantation in such patients to be carefully calculated and/or determined in order to provide the ability to compress to a provide sufficiently small for insertion in relatively small catheters, such as within a 6 or 5 French (Fr) catheter. Although 5 and 6 Fr catheters are disclosed, other-sized catheters are also within the scope of the present disclosure, including catheters smaller than 6 or 5 Fr. Furthermore, the dimensions and features should be selected to present sufficient outward radial force over time to result in post-operative growth of the stent that correlates with the growth of the patient, while still being thin enough and/or otherwise configurable to compress within a 6 or 5 Fr catheter. Therefore, embodiments of the present disclosure provide features relating to the number of circumferential struts, the number of axial rows of struts, the thickness of the stent struts, the axial height of the stent, the circumferential spacing between struts, and/or the like, that advantageously allow for the particular applications for which the respective embodiments are designed. Furthermore, it should be understood that certain dimensions disclosed herein that are designed for particular use in children and infants for whom substantial vascular growth is expected, and are designed in accordance therewith, are not merely trivial or obvious variants of dimensions of stents dimensioned for use in adults and/or other patient for which substantial post-operative vessel growth is not expected, but rather are based on particular combinations of dimensions/features to produce each of the following results: sufficient radial strength to hold open and/or expand a coarctation segment of an aortic vessel, sufficient outward radial self-expansion force to produce post-operation growth expansion, outward radial self-expansion force that is not strong enough to result in propagation/migration of the stent through the target vessel wall, and/or axial height sufficient to cover the desired coarctation region.

When crimped or in a compact/compressed state (e.g., not fully expanded), the stent 200 can produce an outward force based at least in part on the shape and/or thickness of the struts 210. When expanded, the stent 200 can resist contraction caused by inward radial forces applied by the vessel in which it is implanted. In some implementations, the outward radial force of the stent 200 can be based at least in part on, and/or adjustable at least in part through selection of, the radial thickness t of the struts 210. As an example, where the thickness t of the struts 210 is about 0.33 mm, the range of radial forces produced by the stent 200 may be between about 1 N and about 3 N. As another example, where the wall thickness t of the struts 210 is about 0.48 mm, the range of radial forces produced by the stent 200 may be between about 2 N and about 5 N. The range of forces can be tuned or tailored by adjusting the wall thickness of the struts 210, for example. In some embodiments, increasing the wall thickness can increase the radial forces produced by the stent. Different configurations of strut shape, wall thickness, joints, nodes, strut material, and the like can be arranged to alter/determine the range of radial forces generated by the stent 200. The numbers provided herein are merely examples and any other numbers/values may be used within the scope of the present disclosure.

In some embodiments, the wall/radial thickness t of the struts 210 is at least about 0.2 mm and/or less than or equal to about 0.7 mm, at least about 0.25 mm and/or less than or equal to about 0.6 mm, or at least about 0.3 mm and/or less than or equal to about 0.5 mm. In various embodiments, the radial force produced by the stent 200 exceeds at least about 0.5 N, exceeds at least about 0.75 N, exceeds at least about 1 N, exceeds at least about 2 N, or exceeds at least about 3 N. Similarly, the radial force produced by the stent 200 can be less than or equal to about 10 N, less than or equal to about 8 N, less than or equal to about 6 N, less than or equal to about 5 N, or less than or equal to about 3 N.

FIG. 2E illustrates the stent 200 in a crimped or compact state. The profile do of the stent 200 in the crimped state can be less than or equal to 6 French (e.g., less than or equal to about 2 mm). In the crimped state, the stent 200 can experience a maximum principal strain of less than or equal to about 6.27%, or any other percentage. The crimped stent 200 in FIG. 2E advantageously has a profile do that is less than or equal to 2 mm so that it can be implanted percutaneously in certain infant patients, which have relatively small blood vessels compared to older children and adults. In some embodiments, the stent 200 has cloth around the struts 210, or a sleeve of cloth around the circumference of the stent 200, which may serve to promote tissue ingrowth and/or to increase the surface area of the stent and thereby distribute the outward radial force thereof more evenly to prevent the struts of the stent from pushing through the vessel wall. However, as the addition of cloth or other layer(s) or coating to the device can increase the profile of the stent 200, certain embodiments of the stent 200, such as that shown in FIGS. 2A-2E, advantageously do not have cloth or other layer(s)/coating in order to facilitate compression to a profile dimension do that is no greater than 2 mm. Although it is possible to perform minimally-invasive through-chest surgical interventions on young children and infants, due to the relatively fragile physical states of infants with heart-related conditions, interventions requiring general anesthesia may be undesirable or untenable. For example, often infant patients suffering from aortic coarctation also suffer from one or more other conditions and/or complications, and so they may not be fit to tolerate non-percutaneous/transcatheter cardiac surgical interventions.

Therefore, embodiments of the present disclosure having the particular ranges of dimensions and/or number/arrangement of struts disclosed can be safer for certain infant patients.

Figure 3:
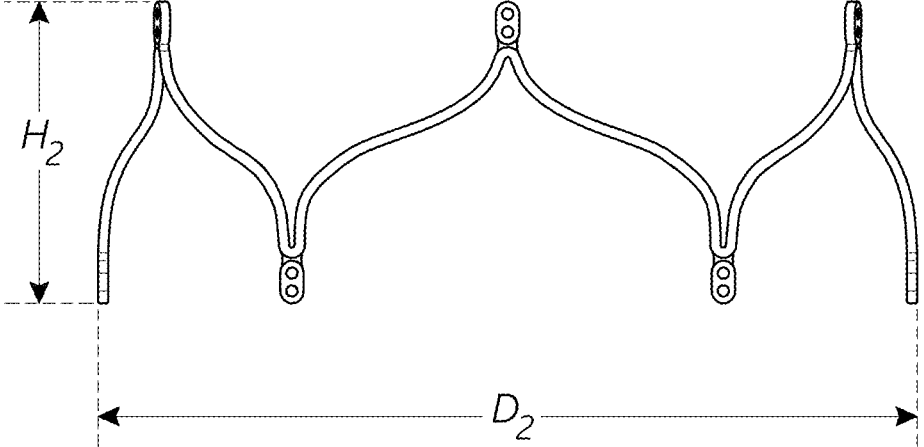
FIG. 3 shows a side view of the stent shown in FIG. 2B in a growth-expansion configuration in accordance with one or more embodiments.

Whereas FIG. 2E shows the stent 200 in a crimped or compressed configuration, which advantageously has a profile do that is sufficiently small (e.g., 2 mm or less) to fit within a delivery system designed to pass through the vasculature of a child or infant, FIGS. 2A-2D shows the stent 200 in an initial expanded configuration having a diameter dimension $D_1$ and FIG. 3 shows the stent 200 in a post-operative growth-expansion configuration after the stent 200 has expanded/grown in diameter to a diameter $D_2$ in connection with natural growth of the blood vessel in which it is implanted after a growth period of time after implantation of the stent. The diameter $D_1$ may be about 10 mm, or any value between about 10-14 mm. In some embodiments, the diameter $D_1$ is about 9 mm, or another value between about 2 mm and 10 mm. In some embodiments, the diameter $D_1$ is about 3 mm. In some embodiments, the diameter $D_1$ is about 4 mm. In some embodiments, the diameter $D_1$ is about 5 mm. In some embodiments, the diameter $D_1$ is about 6 mm. In some embodiments, the diameter $D_1$ is about 7 mm. In some embodiments, the diameter $D_1$ is about 8 mm.

The growth-expansion diameter $D_2$ may be about 20 mm, or any value between 14-20 mm. In some embodiments, the diameter $D_2$ is about 14 mm. In some embodiments, the diameter $D_2$ is about 15 mm. In some embodiments, the diameter $D_2$ is about 16 mm. In some embodiments, the diameter $D_2$ is about 17 mm. In some embodiments, the diameter $D_2$ is about 18 mm. In some embodiments, the diameter $D_2$ is about 19 mm. In some embodiments, the diameter $D_2$ is between about 20-25 mm. In some embodiments, the diameter $D_2$ is greater than about 25 mm. In some embodiments, the diameter $D_2$ is about 25 mm.

The thickness t (see, e.g., FIGS. 2A and 8A) of the body of a sent in accordance with the present disclosure, such as the stent 200, may vary from embodiment to embodiment, but in certain embodiments is between about 0.2-0.3 mm. For example, in a preferred embodiment, the thickness t of the struts 210 is about 0.22 mm, which may provide a suitable balance between outward radial force, strength, and softness/flexibility so as to not push through the vessel wall. For example, a thickness t of about 0.22 mm can produce desirable outward growth-expansion for a stent having strut features, dimensions, arrangement, and/or configuration like the stent 200 shown in FIGS. 2A-2E and FIG. 3. For example, where the thickness t is greater than about 0.22 mm, such as greater than about 0.25 mm, 0.26 mm, 0.27 mm, 0.28, and/or 0.29 mm, such thickness may result in migration of the stent through the arterial wall over time after implantation. Furthermore, where the thickness t is less than about 0.22 mm, such as less than about 0.2 mm, such thickness may result in a softness/flexibility that does not provide enough strength to open the target vessel/coarctation.

In some embodiments, stents in accordance with the present disclosure are cut from a metal (e.g., memory metal) tube having the desired strut thickness. In certain preferred embodiments, radially self-expanding stents comprise and/or are made/cut from Nitinol®. In some embodiments, struts of an example radially self-expanding stent in accordance with aspects of the present disclosure have a thickness t of about 0.2 mm. In some embodiments, struts of an example radially self-expanding stent in accordance with aspects of the present disclosure have a thickness t of about 0.21 mm. In some embodiments, struts of an example radially self-expanding stent in accordance with aspects of the present disclosure have a thickness t of about 0.23 mm. In some embodiments, struts of an example radially self-expanding stent in accordance with aspects of the present disclosure have a thickness t of about 0.24 mm. In some embodiments, struts of an example radially self-expanding stent in accordance with aspects of the present disclosure have a thickness t of about 0.25 mm. The various dimensions disclosed herein in connection with the embodiments of the present disclosure have been determined based on crush tests, radial force tests, and/or other tests/data to determine optimal values and/or ranges of values for dimensions.

For purpose of clarification, the terms "crimped" and "compressed" configurations and states of stents are used according to their broad and ordinary meanings and refer to a configuration or state of a stent having a lowest or substantially-lowest diametrical profile for the stent, or a state or configuration that is in accordance with a delivery profile for transportation within a delivery catheter or sheath. The terms "expanded" and "initial expanded" state and configuration are used according to their broad and ordinary meanings and refer to a configuration or state of a self-expanding stent having a diameter near or equal to that of a target blood vessel (e.g., aortic arch and/or descending aorta of a child or infant) at or immediately after implantation of the stent therein. The terms "growth-expansion," "further-expanded," and "post-operative expansion" configuration and state are used herein according to their broad and ordinary meanings and refer to a state or configuration of a radially self-expanding stent having a diameter greater than that of the stent at or soon after implantation thereof, wherein such diameter expansion is produced or effected at least in part by outward radial force exerted inherently by the stent structure and/or fixation to a vessel that undergoes diametrical growth over a post-operative/implantation period of time. Therefore, radially self-expanding stents in accordance with embodiments of the present disclosure can be considered to be in a growth-expansion or post-implantation-expansion state a growth period of time after implantation in which the diameter of the stent has increased without requiring a post-implantation intervention to achieve or effect such expansion.

The stent 200 can be made of any of various suitable self-expanding materials (e.g., Nitinol®) as known in the art. When constructed of a self-expandable/shape-memory material, the stent 200 can be crimped to a radially compressed state and restrained in the compressed state by insertion into a sheath or equivalent mechanism of a delivery catheter. Once inside the body, the stent 200 can be advanced from the delivery sheath/catheter, which allows the stent 200 to produce radially outward forces to expand and be implanted at the targeted site. The stent 200 can be made from shape memory alloys such as nickel titanium (nickel titanium shape memory alloys, or NiTi, as marketed, for example, under the brand name Nitinol®), or other biocompatible metals.

The stent 200 can have a generally annular or toroidal body, which may be formed at least in part from a suitable shape-memory material (e.g., metal, alloy, etc.), such as spring steel, Elgiloy®, or Nitinol®. In some embodiments, the material from which the stent 200 is fabricated allows the stent to automatically, or at least partially automatically, expand from the compressed/crimped state shown in FIG. 2E to the expanded state shown in FIG. 2D when deployed. Furthermore, the material of the stent 200 can advantageously also allow the stent 200 to be radially compressed to a smaller-profile compressed/crimped configuration similar to that shown in FIG. 2E for delivery through the patient's vasculature. In some embodiments, the stent 200 is not self-expanding, wherein expansion to the post-operative further-expanded configuration is achievable using another expansion mechanism, such as a balloon catheter.

Generally, the stent 200 may have a form or shape as illustrated in FIGS. 2A-2E, defining a number of peaks and valleys (or crests and troughs) along its circumference. For example, the stent 200 can have S-shaped sawtooth struts, as shown in FIGS. 2B-2D, straight sawtooth struts, ringlet-shaped struts, or other-shaped struts forming peaks and valleys. Although the peaks of the stent 200 are shown as pointed, in some embodiments, the stent 200 has a more curved, generally sinusoidal, side profile, wherein the peaks are rounded curves, or the like.

The stent 200 can be sized such that the stent 200 can be positioned within the aorta of a patient at a location at or near the interface between the aortic arch and the descending aorta. With respect to stent embodiments of the present disclosure configured to be utilized as docking structures for securing a prosthetic valve device thereto, such stents may have a diameter that is equal to or smaller than the diameter of the relevant prosthetic heart valve when fully expanded. The joint forms/structures 220 of the stent 200 can serve as arms that facilitate positioning and/or deployment of the stent 200 into in the target position in some implementations. For example, the joint forms/structures 220 may have respective apertures 221.

FIG. 3 shows a side view of the stent 200 of FIGS. 2A-2E in a post-operative further-expanded configuration. For example, the further-expanded configuration of FIG. 3 may provide a post-operative growth-expansion diameter $D_2$ of the stent 200 corresponding to growth in the diameter of the aorta or other vessel in which the stent 200 is implanted. The diameter $D_2$ may be about 20 mm, or any value between 14-20 mm. The various dimensions and features shown in FIGS. 2A-2E and FIG. 3 and described above should be understood to be implementable in any of the embodiments disclosed herein and are not repeated in connection with each of the embodiments disclosed below for the sake of simplicity and clarity.

Although various embodiments of stents are disclosed herein in the context of aortic-coarctation-correction stents, stents in accordance with the present disclosure may further be used as docking devices for prosthetic heart valve implant devices in children and infants expected to experience substantial post-operative growth of a native target valve annulus. For example, for children and infants suffering from aortic valve disfunction for which a replacement prosthetic heart valve is desirable, a docking stent may be desirable due to the general lack of calcification formation in the aorta that might otherwise at least partially secure the valve in the aortic annulus.

Figure 4A:
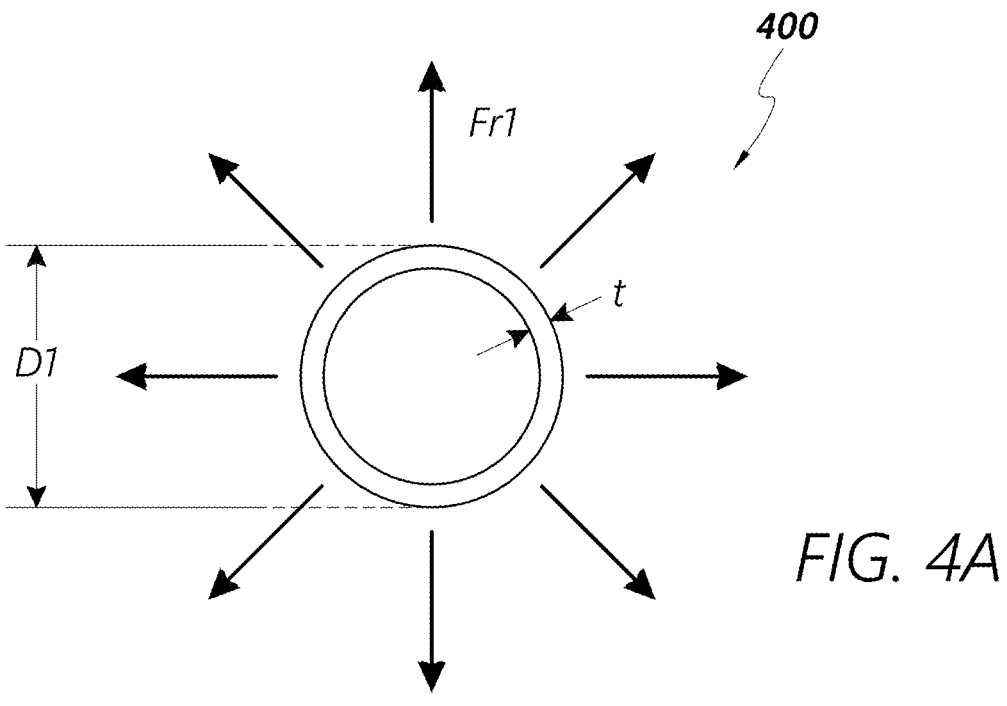
FIGS. 4A and 4B illustrate axial views of an example radially self-expanding stent at two different diameters producing outward radial forces according to one or more embodiments.
Figure 4B:
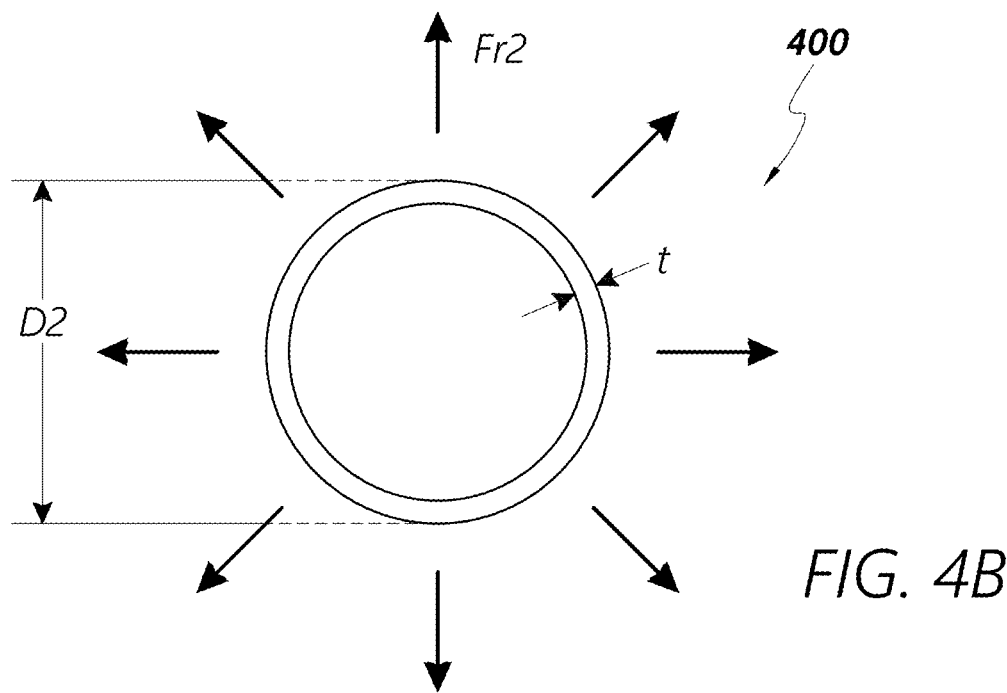

FIGS. 4A and 4B illustrate top views of an example of a radially self-expanding stent 400 at two different sizes, namely an initial expanded state/size and a post-operative growth expansion state/size, a compressed state/size and an initial expanded state/size, or a compressed size/state and a post-operative growth expansion state/size. In some embodiments, the stent 400 expands from a diameter $D_1$ to a diameter $D_2$, where diameter $D_1$ can be less than or equal to about 2 mm and the diameter $D_2$ can be at least about 20 mm, or any value in between these. For each diameter $D_1$, $D_2$, the stent is configured to produce an outward radial force, $Fr_1$, $Fr_2$, respectively. In some embodiments, in addition to depending on the wall thickness of the struts, the radial force depends at least in part on the current diameter of the stent 400. For example, as the diameter increases to a maximum operating diameter or post-operative growth expansion diameter, the radial force can decrease. The relationship between the diameter and the radial force can be a function of the wall thickness of the struts, the shape of the struts, the joints, the nodes, the material of the struts, and the like. Thus, the relationship between the diameter and the radial force can be a complicated function and need not be monotonically related.

Figure 5:
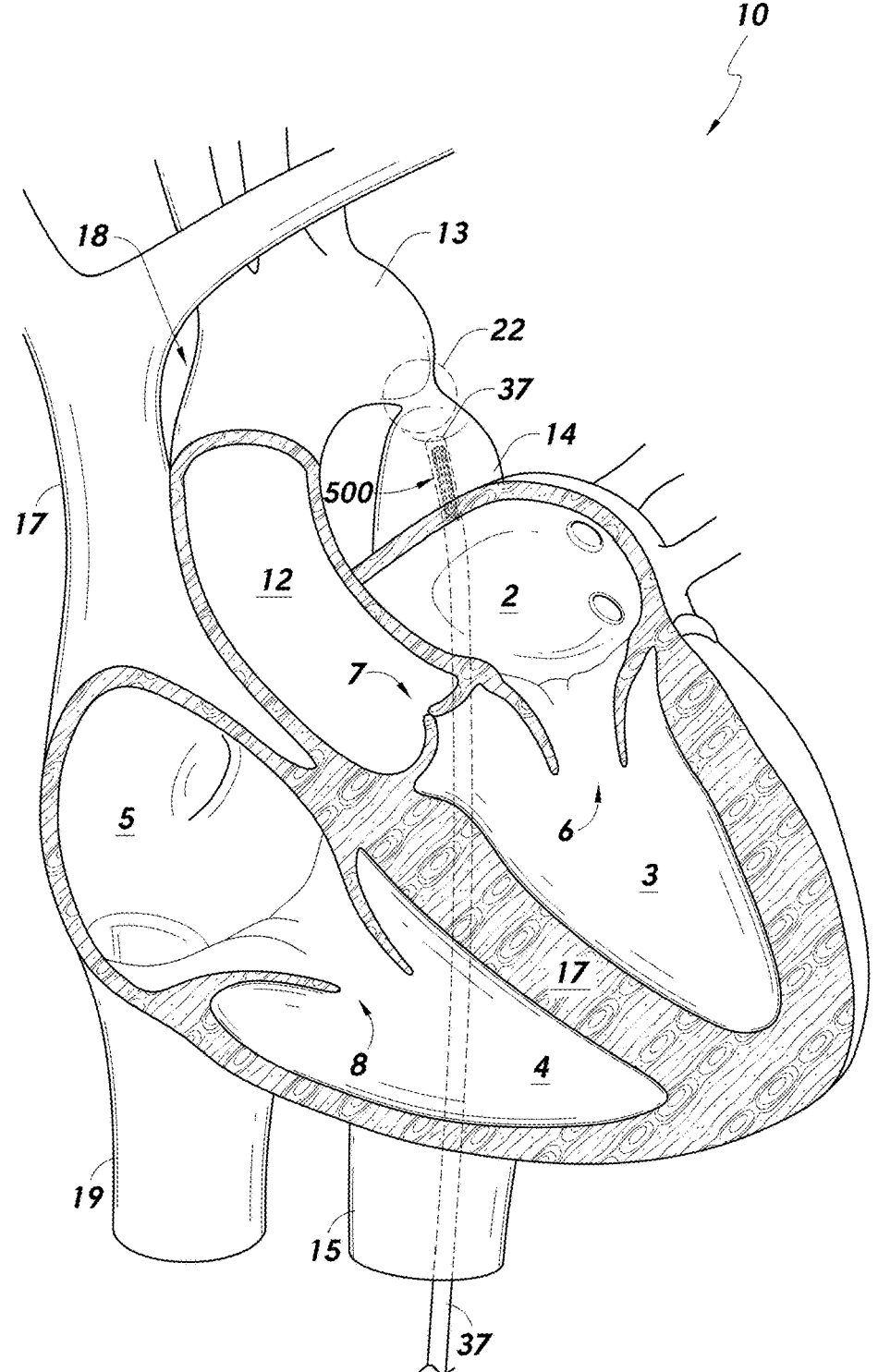
FIG. 5 illustrates a partial cross-sectional view of cardiac anatomy with a delivery system disposed in aortic anatomy thereof.

FIG. 5 illustrates a partial cross-sectional view of cardiac anatomy 10 with a delivery system 37 disposed in aortic anatomy 18 thereof. Rather than accessing the aortic anatomy through an open-chest or other invasive surgical procedure, radially self-expanding stents in accordance with embodiments of the present disclosure can advantageously be implanted in, for example, children and/or infants using a transcatheter procedure to access an area of aortic coarctation through the arterial and/or venous system(s). Such procedures can be done through very small openings that leave all the chest bones in place. Furthermore, transcatheter access can result in a relatively faster recovery in most cases. However, transcatheter procedures can present certain challenges for small patients, such as infants and small children. For example, the relatively small arteries and/or veins can be difficult to navigate and can require particularly small catheters, and therefore small implant devices that can fit in such catheters.

As shown in FIG. 5, a delivery catheter 37 may be advanced to a target coarctation 22 through the aortic anatomy. For example, the catheter 37 may enter through the femoral artery according to a transfemoral approach, which does not require a surgical incision in the chest. As an alternative, the approach to the aorta may be made through the venous system (e.g., femoral vein and/or inferior vena cava), wherein the access path crosses over into the arterial system at or near the abdominal aorta. The delivery catheter 37 may advantageously be a 6 French catheter, or smaller, for navigation in a relatively small vasculature.

Generally, for radially self-expanding stents in accordance with aspects of the present disclosure that are not used also as docking device, the fluid forces that such stents may be subject primarily to may only include pulse pressure force from blood flow therein. The target location for implantation of the radially self-expanding stent 500 may be in and/or near the relatively straight descending portion 14 of the aorta.

After implantation of the stent 500, the friction-fit of the stent 500 with the aortic wall may be sufficient to maintain the stent 500 in the desired position/location. Generally, where too much tissue overgrowth has occurred over the stent frame, such tissue growth may undesirably lock the stent in its current configuration, thereby preventing the stent 500 from growing post-operatively as the patient's anatomy grows. Therefore, although some embodiments can include a sealing skirt/layer comprising cloth, such components can result in undesirable tissue growth. Therefore, in some embodiments, no sealing skirt/cloth is included, at the expense of sacrificing sealing functionality. Although embodiments of the present disclosure are disclosed in the context of corrective devices for correcting aortic coarctation, some embodiments of the present disclosure can serve as mitral valve docking devices for disposal in the native mitral valve annulus. For example, rheumatic fever in young patients can cause damage to mitral leaflets. Therefore, radially self-expanding stents in accordance with aspects of the present disclosure can provide post-operatively growing mitral valves and/or mitral valve docking stents.

Figure 6:
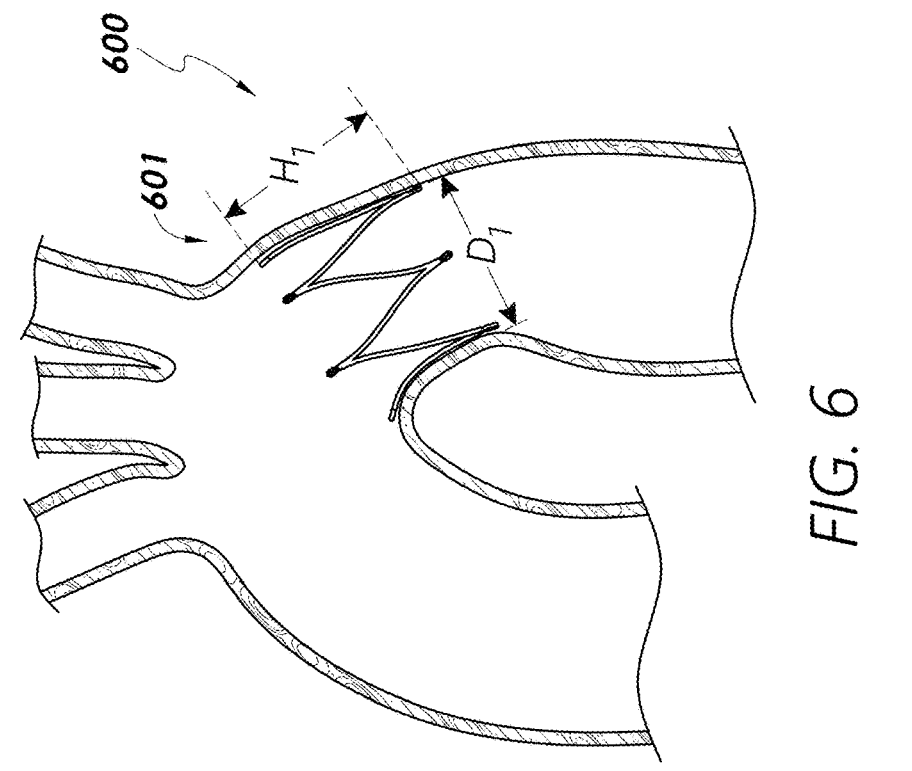
FIG. 6 shows a radially self-expanding stent implanted in vascular anatomy in an expanded configuration in accordance with embodiments of the present disclosure.

FIG. 6 shows an anatomical vessel 601, such as a portion of an aorta, having a radially self-expanding stent 600 implanted therein in accordance with one or more embodiments of the present disclosure. In the image of FIG. 6, the stent 600 is in an initial expanded state with a diameter $D_1$, which may represent a diameter of the stent 600 that is near or equal to that of the blood vessel 601 (e.g., aortic arch and/or descending aorta of a child or infant) at or immediately after implantation of the stent 600 therein.

Figure 7:
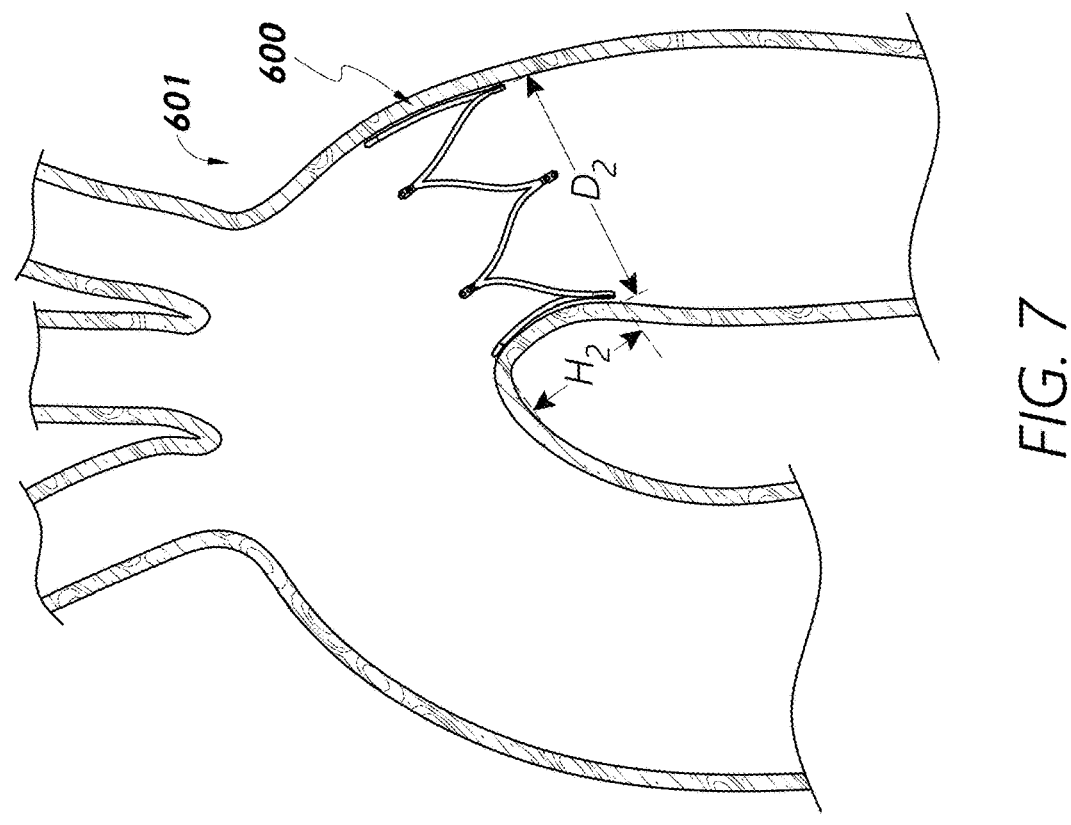
FIG. 7 shows a radially self-expanding stent implanted in vascular anatomy in a growth-expansion configuration in accordance with embodiments of the present disclosure.

FIG. 7 shows the anatomical vessel 601 and radially self-expanding stent 600 of FIG. 6 in an at least partially further-expanded state relative to the respective configuration/state shown in FIG. 6. In the image of FIG. 7, the stent 600 is in a partially- or fully-expanded state with a diameter $D_2$ that is greater than the diameter $D_1$. That is, the configuration of the stent 600 in FIG. 7 is a post-operative growth-expansion configuration, wherein the radially self-expanding stent 600 has a diameter $D_2$ greater than that of the stent 600 at or soon after implantation thereof, wherein such diameter expansion is produced or effected at least in part by outward radial force exerted inherently by the stent structure 600 and/or fixation to the vessel 601 that undergoes diametrical growth over a post-operative/implantation period of time. For example, the configuration of the stent 600 in FIG. 7 may represent a post-implantation expansion state a period of time after implantation in which the diameter of the stent 600 has increased without requiring a post-implantation intervention to achieve or effect such expansion.

Due to the bending and expansion of the struts of the stent 600 in connection with expansion from the diameter $D_1$ to the diameter $D_2$, the height of the stent 600 may be reduced from the deployed height $H_1$ to the post-operative expansion height $H_2$ shown in FIG. 7. Generally, the height $H_2$ of the stent 600 in the growth-expansion state may be less than the height $H_1$ in the initial expanded state of the stent 600 shown in FIG. 6.

The growth expansion of the radially self-expanding stent 600 may be due at least in part to substantially constant radial force exerted by the stent structure due to shape memory characteristics thereof, as described in detail herein. Furthermore, in some implementations, the struts of the stent 600 may become overgrown by endothelial tissue growth over time after implantation of the stent. Such tissue growth may serve to at least partially secure the stent structure to the vessel wall, which may further exert outward radial force on the stent as the vessel grows, thereby causing expansion in the stent post-operatively based on the particular strut dimensions, configuration, and arrangement of the stent 600. In some embodiments, the stent 600 is configured to present an optimum outward radial force that it is sufficient to at least partially break or disrupt endothelial tissue overgrowth to a degree that the tissue overgrowth does not prevent further post-operative expansion of the stent caused by the shape memory characteristics thereof, at least for an initial post-operative phase (e.g., about 90 days).

Although not shown in FIGS. 6 and 7, in some implementations, a sleeve or fabric/cloth is disposed around at least a portion of the stent frame/structure to increase surface area of the stent frame/structure. Furthermore, the number of circumferentially-arranged struts around a circumference of the stent 600 can be increased beyond what is shown in FIGS. 2A-2E to provide a relatively safer stent with regards to risk of migration through the arterial wall. For example, although 12 circumferentially-arranged struts are shown in the embodiment(s) of FIGS. 2A-2E, in some embodiments, 14, 16, 18, or 20 circumferentially-arranged struts are implemented in a radially self-expanding stent in accordance with the present disclosure.

Figure 8A:
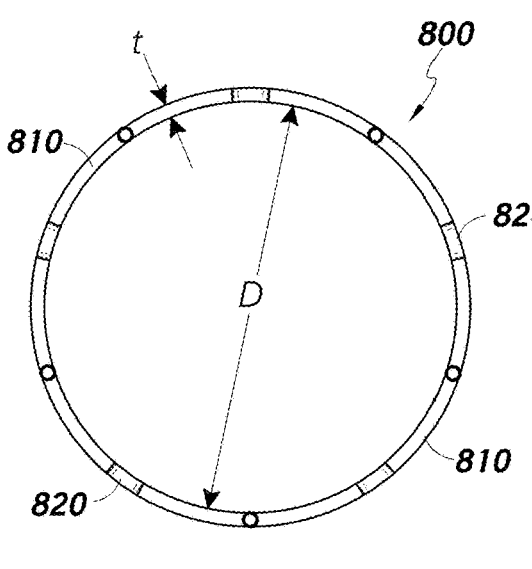
FIG. 8A illustrates an axial view of an example radially self-expanding stent in accordance with one or more embodiments.
Figure 8C:
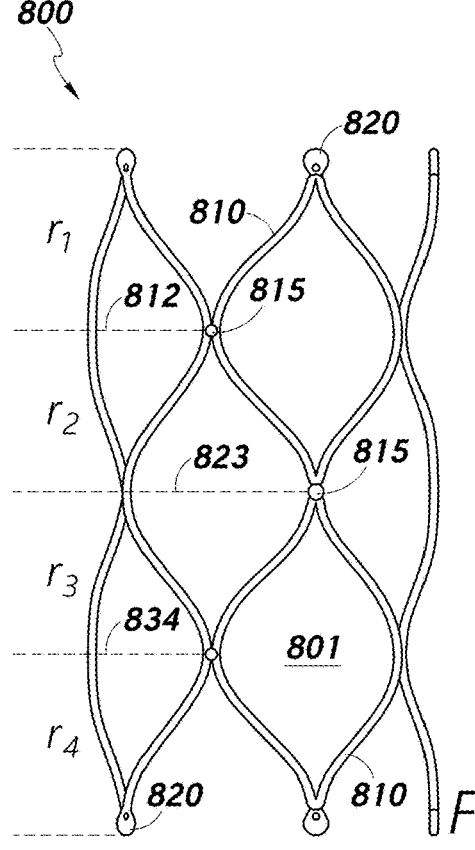
FIGS. 8B and 8C illustrate side views of an example radially self-expanding stent like that shown in FIG. 8A in accordance with one or more embodiments.
Figure 8B:
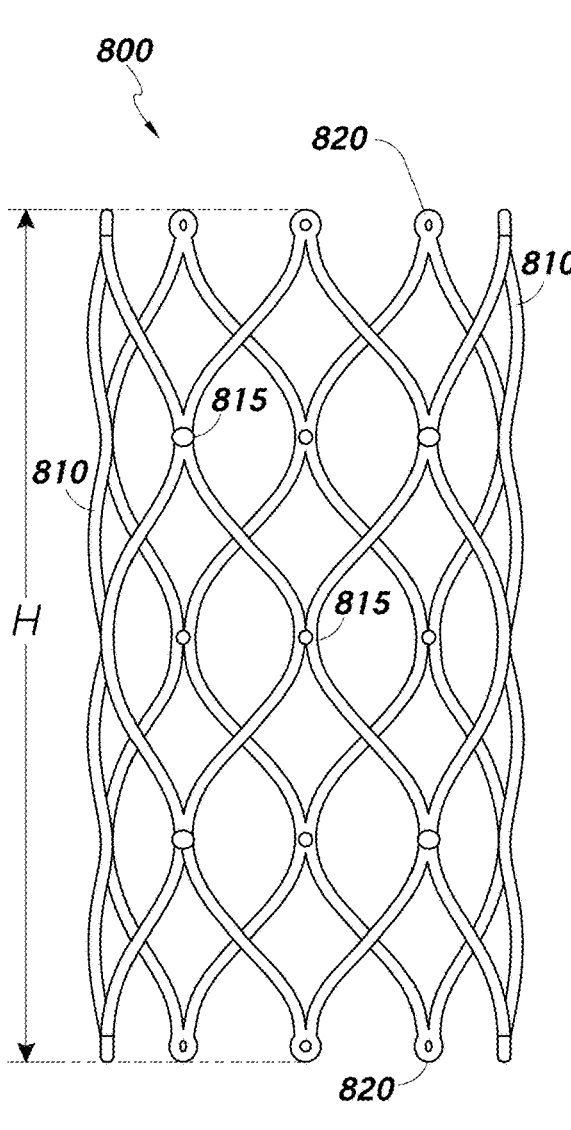

FIGS. 8A-8C illustrate another example of a radially self-expanding stent 800 that has a larger height H than the stent 200 of FIGS. 2A-2E. The stent 800 is in a net-like configuration with repeating curved struts 810 mirrored about axial strut row interfaces 812, 823, 834 along its height (e.g., from a proximal to a distal ends) that are joined together at proximal and distal ends at joints 820 and along its height at junctions or nodes 815.

The larger height H of stent 800 can be achieved using struts 810 that are joined together at proximal and distal ends using joints 820, as in the stent 200, but can include struts 810 that are longer, repeating a curved pattern. For example, as shown, the struts can form axially-arranged rows, wherein the nodes 815 lie at the interfaces between the rows. The longer struts 810 can be joined to adjacent struts at the junctions or nodes 815 between the proximal and distal end joints 820. In some embodiments, the struts 810 can be formed from shapes similar to the shapes of the stent 200 of FIGS. 2A-2E that are joined together end-to-end at junctions or nodes 815. In such embodiments, the nodes 815 can be configured to join adjacent struts 810 to one another.

Whereas the stent 200 shown in FIGS. 2A-2E and 3, and described in detail above, comprises a single axial row of struts, it should be understood that radially self-expanding stents in accordance with the present disclosure can have any suitable or desirable number of axial rows of struts. For example, the stent 800 of FIGS. 8A-8C includes four axial rows (r₁, r₂, r₃, r₄) disposed between axially adjacent junctions/nodes 815 and/or joints 820. Generally, a greater number of axial rows of struts may produce a greater height H dimension for the stent, which may advantageously support a relatively longer length of blood vessel. The number of axial rows of struts can affect the outward radial force of the stent, such that a stent with more than one row may provide more outward radial force than a single-row stent having similar material, thickness, and strut features. Therefore, in some implementations, the stent 800 may have thinner struts than those of the stent 200, while providing similar or greater radial force/growth characteristics. Axially-mirrored stents can form cells 801, as shown.

By way of example, the diameter D of the stent 800 can vary between about 2 mm and about 20 mm. The height H of the stent 800 can vary between about 20 mm and about 42 mm. The wall thickness of the struts 810 can be about 0.33 mm in some embodiments. In this example configuration, the range of radial forces produced by the stent 800 can be between about 15 N and about 20 N. Different configurations of strut shape, wall thickness, joints, nodes, strut material, and the like can be arranged to alter the range of radial forces generated by the stent 800. The numbers provided herein are merely examples.

In some embodiments, the wall thickness of the struts 810 is at least about 0.2 mm and/or less than or equal to about 0.7 mm, at least about 0.25 mm and/or less than or equal to about 0.6 mm, or at least about 0.3 mm and/or less than or equal to about 0.5 mm. In various embodiments, the radial force produced by the stent 800 exceeds at least about 8 N, exceeds at least about 7.5 N, exceeds at least about 10 N, exceeds at least about 12 N, or exceeds at least about 15 N. Similarly, the radial force produced by the stent 800 is less than or equal to about 30 N, less than or equal to about 27 N, less than or equal to about 25 N, less than or equal to about 22 N, or less than or equal to about 20 N.

Having more rows of struts as in the stent 800 of FIGS. 8A-8C, and therefore more cells 801, can produce greater stiffness. Therefore, the stent 800 may have suitable stiffness for providing docking functionality for a prosthetic valve device. That is, docking stents for valve devices often require relatively stronger stents/struts due to the forces presented at the valve leaflet commissure regions. Such forces can produce torque on the struts of the stent, and therefore may require greater stiffness/strength.

In some implementations, the outward radial force of the stent 800 can be based at least in part on, and/or adjustable at least in part through selection of, the radial thickness t of the struts 810. As an example, where the thickness t of the struts 810 is about 0.33 mm, the range of radial forces produced by the stent 800 may be between about 1 N and about 3 N. As another example, where the wall thickness t of the struts 810 is about 0.48 mm, the range of radial forces produced by the stent 800 may be between about 8 N and about 5 N. The range of forces can be tuned or tailored by adjusting the wall thickness of the struts 810, for example. In some embodiments, increasing the wall thickness can increase the radial forces produced by the stent. Different configurations of strut shape, wall thickness, joints, nodes, strut material, and the like can be arranged to alter/determine the range of radial forces generated by the stent 800. The numbers provided herein are merely examples.

Figure 9:
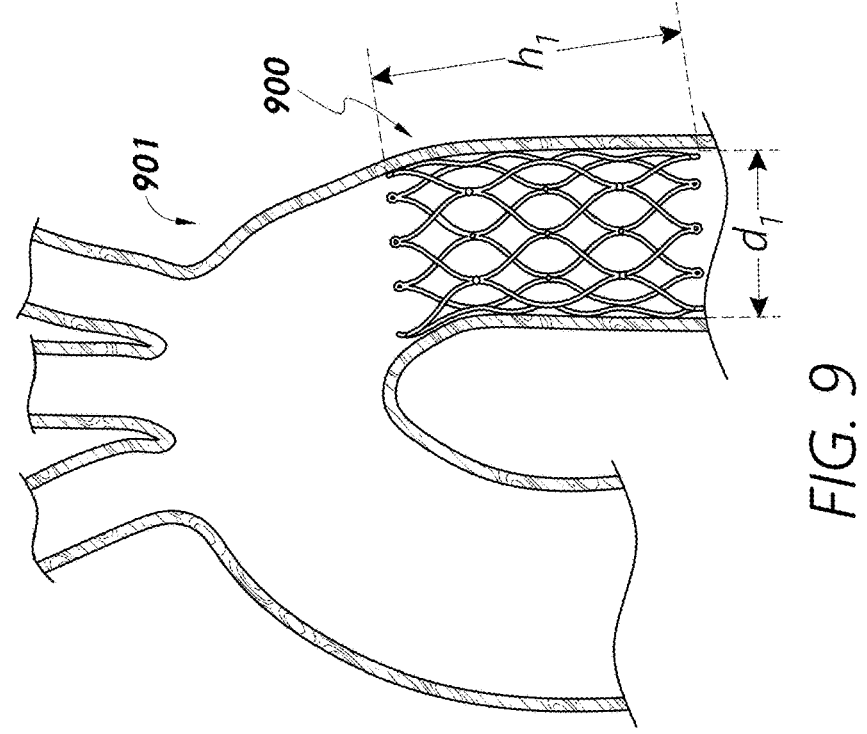
FIG. 9 shows a radially self-expanding stent implanted in vascular anatomy in an expanded configuration in accordance with one or more embodiments.

FIG. 9 shows an anatomical vessel, such as a portion of an aorta, having a multiple-row radially-expandable stent 900 implanted therein in accordance with one or more embodiments of the present disclosure. In the image of FIG. 9, the stent 900 is in a partially-expanded state with a diameter d₁, which represents a diameter of the stent 900 that is near or equal to that of the blood vessel 901 (e.g., aortic arch and/or descending aorta of a child or infant) at or immediately/soon after implantation of the stent 900 therein.

Figure 10:
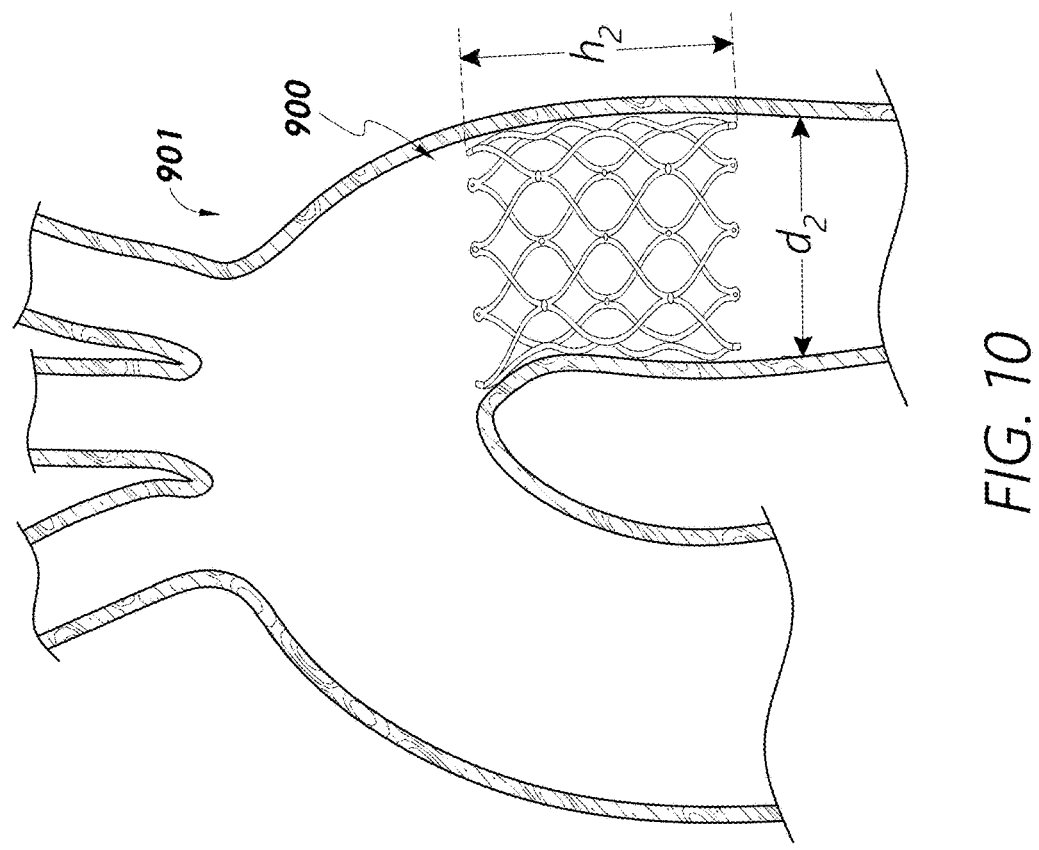
FIG. 10 shows a radially self-expanding stent implanted in vascular anatomy in a growth-expansion configuration in accordance with one or more embodiments.

FIG. 10 shows the anatomical vessel 901 and radially-expandable stent 900 of FIG. 9 in an at least partially expanded states relative to the respective configurations/states shown in FIG. 9. In the image of FIG. 10, the stent 900 is in a partially- or fully-expanded state with a diameter d₂ that is greater than the diameter d₁. That is, the configuration of the stent 900 in FIG. 10 is a post-operative growth-expansion configuration, wherein the radially self-expanding stent 900 has a diameter d₂ greater than that of the stent 900 at or soon after implantation thereof, wherein such diameter expansion is produced or effected at least in part by outward radial force exerted inherently by the shape memory characteristics of the stent structure 900 and/or fixation to the vessel 901 that undergoes diametrical growth over a post-operative/implantation period of time. For example, the configuration of the stent 900 in FIG. 10 may represent a post-implantation-expansion state a period of time after implantation in which the diameter of the stent 900 has increased without requiring a post-implantation intervention to achieve or effect such expansion.

Due to the bending and expansion of the struts of the stent 900 in connection with expansion from the diameter d₁ to the diameter d₂, the height of the stent 900 may be reduced from the deployed height h₁ to the post-operative expansion height h₂ shown in FIG. 10. Generally, the height h₂ of the stent 900 in the growth-expansion state may be less than the height h₁ in the initial expanded state of the stent 900 shown in FIG. 9.

The growth expansion of the radially self-expanding stent 900 may be due at least in part to substantially constant radial force exerted by the stent structure due to shape memory characteristics thereof, as described in detail herein.

Furthermore, in some implementations, the struts of the stent 900 may become overgrown by endothelial tissue growth over time after implantation of the stent. Such tissue growth may serve to at least partially secure the stent structure to the vessel wall, which may further exert outward radial force on the stent as the vessel grows, thereby causing expansion in the stent post-operatively based on the particular strut dimensions, configuration, and arrangement of the stent 900. In some embodiments, the stent 900 is configured to present an optimum outward radial force that it is sufficient to at least partially break or disrupt endothelial tissue overgrowth to a degree that the tissue overgrowth does not prevent further post-operative expansion of the stent caused by the shape memory characteristics thereof, at least for an initial post-operative phase (e.g., about 90 days).

Although not shown in FIGS. 9 and 10, in some implementations, a sleeve or fabric/cloth is disposed around at least a portion of the stent frame/structure to increase surface area of the stent frame/structure. Furthermore, the number of circumferentially-arranged struts around a circumference of the stent 900 can be increased beyond what is shown in FIGS. 8A-8C to provide a relatively safer stent with regards to risk of migration through the arterial wall. For example, although 10 circumferentially-arranged struts for each row of struts are shown in the embodiment(s) of FIGS. 8A-8C, in some embodiments, 8, 12, 14, 16, or 18 circumferentially-arranged struts are implemented in a radially self-expanding stent in accordance with the present disclosure. Compared to the stent 200 of FIGS. 2A-2E, which is described as having 12 circumferentially-arranged struts in a single axial row in some embodiments, due to the increased mechanical strength of the stent 800 based at least in part on the greater number of axial rows of struts, similar or greater overall radial strength/support may be provided by the stent 800 in spite of the fact that it may have fewer circumferentially-arranged struts per axial row.

Figure 11:
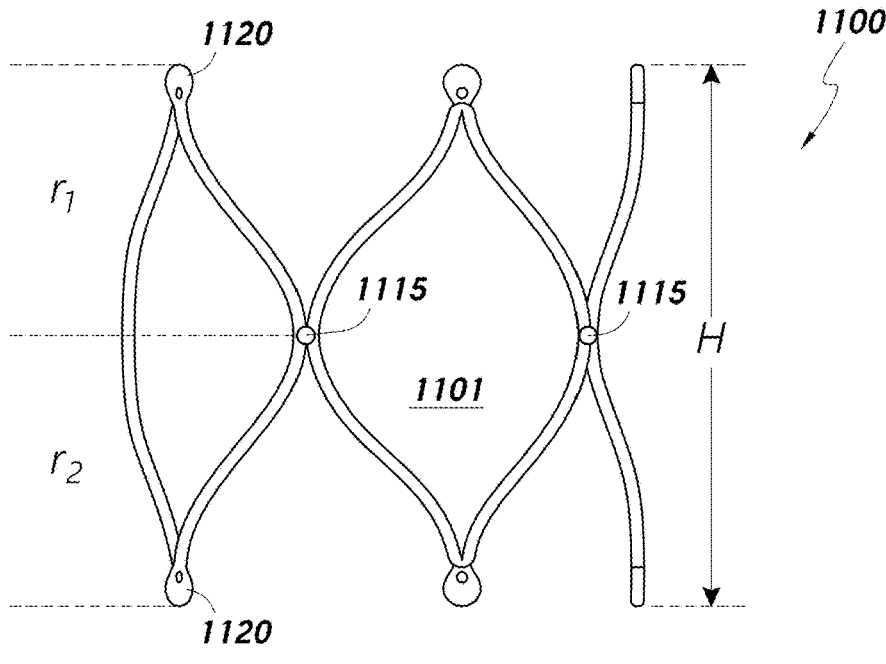
FIG. 11 is a side view of a radially self-expanding stent in accordance with one or more embodiments.

FIG. 11 is a side view of a radially self-expanding stent 1100 in accordance with one or more embodiments. The stent 1100 comprises multiple axial rows of struts. However, it should be understood that radially self-expanding stents in accordance with the present disclosure can have any suitable or desirable number of axial rows of struts. In FIG. 11, the stent 1100 includes two axial rows ($r_1$, $r_2$) disposed between axially adjacent junctions/nodes 1115 and joints 1120. Generally, having more than one axial row of struts may produce a greater height H dimension for the stent 1100 compared to certain single-row embodiments, which may advantageously support a relatively longer length of blood vessel. The height value H may be between about 14-20 mm or between about 20-42 mm. The number of axial rows of struts can affect the outward radial force of the stent, such that a stent with more than one row may provide more outward radial force than a single-row stent having similar material, thickness, and strut features. Therefore, in some implementations, the stent 1100 may have thinner struts that those of the single-row stent 200 of FIGS. 2A-2E, while providing similar radial force/growth characteristics. Axially mirrored stents can form cells 1101, as shown. In some embodiments, the stent 1100 has struts having a thickness of about 0.30-0.34 mm (e.g., 0.32 mm) and providing outward radial force of about 1-3 N, 3-15 N, or 15-20 N. In some embodiments, the stent 1100 has struts having a thickness of about 0.45-0.5 mm (e.g., 0.48 mm) and providing outward radial force of about 2-5 N, 5-15 N, or 15-20 N. In some embodiments, the stent 1100 has a full diameter of about 20 mm and can crimp down to about 2 mm or less.

Figure 12:
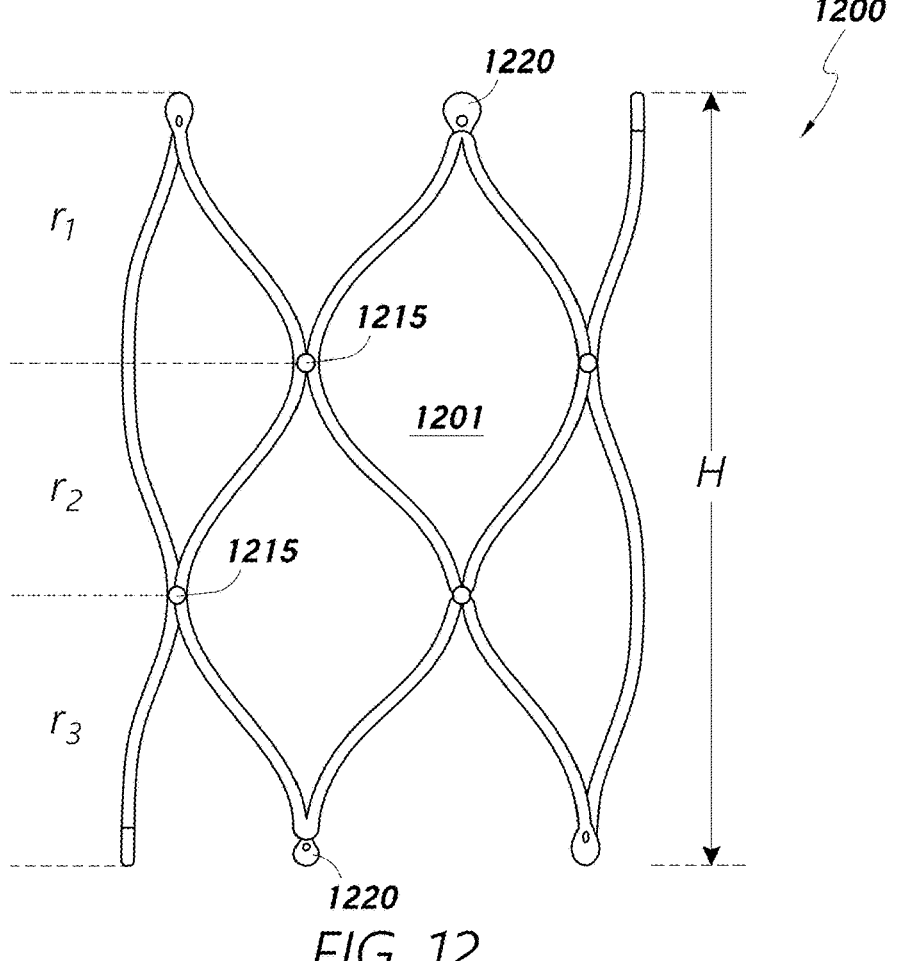
FIG. 12 is a side view of a radially self-expanding stent in accordance with one or more embodiments.

FIG. 12 is a side view of a radially self-expanding stent in accordance with one or more embodiments. The stent 1200 comprises multiple axial row of struts. However, it should be understood that radially self-expanding stents in accordance with the present disclosure can have any suitable or desirable number of axial rows of struts. In FIG. 12, the stent 1200 includes three axial rows ($r_1$, $r_2$, $r_3$) disposed between axially adjacent junctions/nodes 1215 and/or joints 1220. Generally, having more than one axial row of struts may produce a greater height H dimension for the stent 1200 compared to certain single-row embodiments, which may advantageously support a relatively longer length of blood vessel. The height value H may be between about 14-20 mm or between about 20-42 mm. The number of axial rows of struts can affect the outward radial force of the stent, such that a stent with more than one row may provide more outward radial force than a single-row stent having similar material, thickness, and strut features. Therefore, in some implementations, the stent 1200 may have thinner struts that those of the single-row stent 200 of FIGS. 2A-2E, while providing similar or greater radial force/growth characteristics.

Axially-mirrored stents can form cells 1201, as shown. In some embodiments, the stent 1200 has struts having a thickness of about 0.30-0.34 mm (e.g., 0.32 mm) and providing outward radial force of about 1-3 N, 3-15 N, or 15-20 N. In some embodiments, the stent 1200 has struts having a thickness of about 0.45-0.5 mm (e.g., 0.48 mm) and providing outward radial force of about 2-5 N, 5-15 N, or 15-20 N. In some embodiments, the stent 1200 has a full diameter of about 20 mm and can crimp down to about 2 mm or less.

With respect to any of the radially self-expanding stent embodiments disclosed herein, in some situations, relatively less forceful outward force from shape memory characteristics may be preferable to avoid vessel damage and/or outgrowth through the vessel wall. For example, although the disclosed embodiments can be configured to produce about 5 N of radial outward force, configurations providing about 3 N of radial outward force may be preferable in some situations/patients. To achieve the desired force, adjustment to strut thickness may be made between about 0.5 mm (e.g., about 0.48 mm) down to about 0.3 mm (e.g., about 0.33 mm). Although preferred embodiments comprise shape memory metal for producing the desired outward radial force, in some embodiments, outward radial force may be produced by elastic restoration force of a spring-type stent.

The self-expanding shape memory characteristics of embodiments of the present disclosure advantageously obviate the need for subsequent intervention(s) to expand the stent. For example, in certain solutions, a stent may be implanted in a blood vessel, after which the stent may be expanded further subsequently using a balloon when the patient is older. However, such additional subsequent procedure(s) can present risks and discomfort for the patient. The embodiments of the present disclosure can advantageously include curved struts, as described in detail herein (e.g., S-curve struts), that allow the stent to be crimped to a relatively low-profile, such as 2 mm or less, without breaking the struts. For example, for embodiments comprising generally straight struts, the concentration of force on the struts can result in damage at joints/juncture points associated therewith over time.

FIGS. 13 and 14 show partial cross-sectional views of example deployment systems 1300, 1400 for deploying radially-expanding stents. FIGS. 13 and 14 show respective stents 180 and 190 in a compressed/crimped configuration during a pre-deployment stage of a delivery process. The delivery apparatus 1300 comprises an outer catheter/sheath 140 having an elongated shaft, whose distal end 150 is open in the illustrated embodiment. The catheter/sheath 140 may have a relatively small profile dimension pi for navigation in the vascular system of a child or infant. In some embodiments, the catheter/sheath 140 has a profile in accordance with a 6 French size and/or approximately 3 mm in distance.

A proximal end (not shown) of the illustrated delivery systems 1300, 1400 can be connected to or otherwise associated with a handle of the respective delivery apparatus. During delivery of a stent, the handle can be used by a surgeon to advance and retract the delivery apparatus through the patient's vasculature. Radially-expanding stents in accordance with embodiments of the present disclosure may advantageously be advanced through the aorta to or near the aortic arch of the patient's heart in the retrograde direction after having been percutaneously inserted through, for example, the femoral artery. The delivery systems 1300, 1400 can be configured to be selectively steerable or bendable to facilitate advancement of the delivery systems through the patient's vasculature.

The delivery systems 1300, 1400 may also include certain inner shafts and/or pushers or other deployment devices for facilitating stent deployment. In the embodiment of FIG. 13, the delivery system 1300 includes an inner pusher 142 positioned in the interior of the outer sheath 140. The pusher 142 can be configured to be moveable axially relative to the outer sheath 140. A guide wire (not shown) can be inserted into the interior of the pusher 142 and/or outer shaft 140. The guide wire can be used, for example, to help ensure proper advancement of the delivery system and its interior device(s) through the vasculature of the patient.

In the embodiment of FIG. 14, the delivery system 1400 includes an elongated shaft 191 and a stent retaining mechanism 195 connected to a distal end portion of the shaft 191. The shaft 191 of the stent delivery system 1400 can be configured to be moveable axially relative to the outer sheath 192. The stent retaining mechanism 195 can comprise one or more arms. The arms can include distal prongs that may include stent-engagement features, such as features configured to engage apertures in the joints of the stent 190.

The stents 180, 190 are shown in radially-compressed states in the interior of respective sheaths 140, 190. In the radially compressed states, the height of the stents is advantageously greater than the diameter/profile thereof. To deploy the stent 190 in FIG. 14 (i.e., advance the stent 190 from the delivery system 1400), the stent retention component 195 can be advanced toward the distal end 151 of the system 1400 using one or more control handles or mechanisms (not shown) located at the proximal end of the system. This action can cause the stent 190 to be advanced outwardly through the distal end 151 of the system and expand into its expanded, uncompressed state.

The delivery systems 1300, 1400 can be advanced to the aortic arch or other aortic anatomy into a position at or near an aortic coarctation. The delivery systems 1300, 1400 can be inserted through, for example, the femoral artery of the patient and advanced into the aorta in the retrograde direction. Although aortic interventions are disclosed extensively herein, it should be understood that pulmonary interventions may be implemented using embodiments of the present disclosure. In some embodiments, the stent(s) 180 and/or 190 can include one or more barbs or other tissue-engagement features that serve to affix the stent(s) to the tissue surrounding the stent(s).

Treatment Processes Implementing Radially-Expanding Stents

Figure 15:
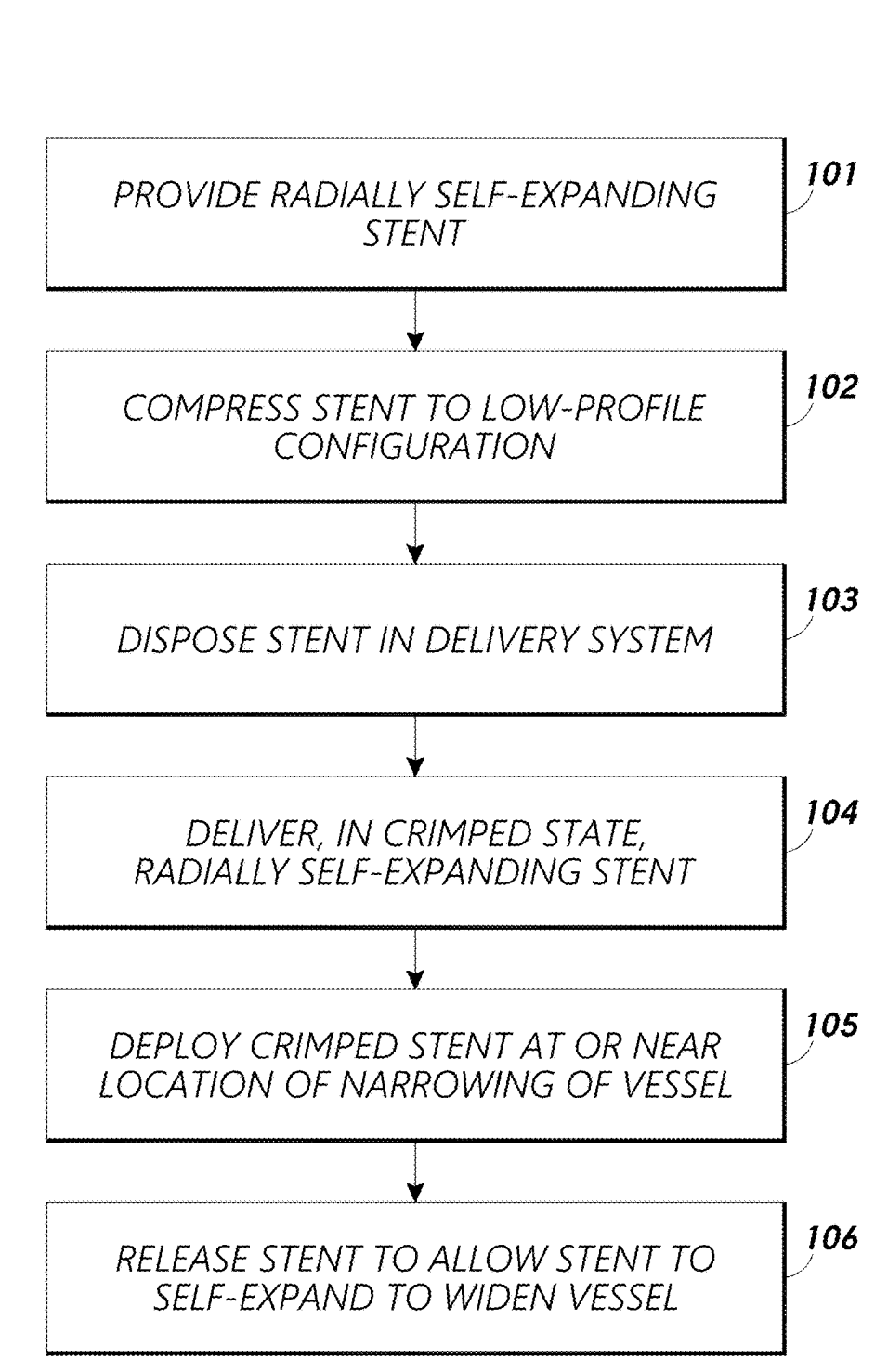
FIG. 15 illustrates a flow diagram of an example method for treating aortic coarctation with any of the radially self-expanding stents described herein.

FIG. 15 illustrates a flow chart of an example process 100 for treating aortic coarctation with any of the radially self-expanding stents described herein. The process 100 can be used to treat any patient with aortic coarctation but may be particularly suitable for patients weighing less than about 10 kg. The implanted stent may be particularly advantageous for this class of patients due at least in part to the stent being configured to operate at relatively small compressed diameters (e.g., about 2 mm) and to the stent being configured to continue to operate as the vessel (e.g., the aorta) increases in size. The increase in size can be caused by the radially outward forces applied by the stent and/or by the growth of the patient.

At block 101, the process 100 involves providing a radially self-expanding stent in accordance with one or more embodiments of the present disclosure. For example, the stent may have any configuration described herein with respect to the number of axial rows of struts, struct thickness, material, strut shape, stent height, outward radial force, and/or maximum stent diameter.

At block 102, the process 100 involves crimping or otherwise compressing the stent into a low-profile configuration. Crimping/compressing the stent may involve compressing the stent to a profile that is less than or equal to about 2 mm in order to fit within a catheter designed for a child's and/or infant's vasculature.

At block 103, the process 100 involves disposing the crimped/compressed stent in a delivery catheter. The compressed stent may be maintained in the delivery catheter in any suitable or desirable way. Example delivery systems and/or configurations are shown in FIGS. 13 and 14, which are described in detail above.

At block 104, the process 100 involves delivering the radially self-expanding stent in the crimped/compressed state through vasculature of the patient in the delivery system. The stent can be constrained at a reduced diameter (e.g., less than or equal to about 5 or 6 French) by a sheath, catheter or other similar structure of the delivery system.

At block 105, the process 100 involves deploying the stent at least in part by removing the catheter/sheath. Removing the catheter/sheath allows the stent to begin to self-expand to an increased diameter. Removal of the catheter/sheath may be facilitated by a pusher or other device associated with the delivery system. The stent is configured to expand to contact the inner walls of the vessel at a targeted location (e.g., at or near the narrowing of the aorta). The targeted location can be upstream or downstream of the narrowing of the aorta or it can be at the narrowing of the aorta, at least in part.

At block 106, the stent is released to allow the radial self-expansion of the stent to begin to widen the vessel at the targeted location. The implanted stent can work over time to widen the vessel to reduce or eliminate the deleterious effects caused by the narrowing of the vessel, such as with aortic coarctation. Advantageously, the method 100 can be used with a pediatric patient and, due at least in part to the structure of the stent causing radially outward forces over a range of diameters, another stent may not need to be implanted to treat aortic coarctation, for example, as the patient grows.

In some embodiments, two or more stents can be implanted using the method 100. For example, a first stent can be implanted at the narrowing of the aorta and a second stent can be implanted upstream or downstream of the first stent. As another example, a first stent can be implanted upstream of the narrowing of the aorta and a second stent can be implanted downstream of the narrowing of the aorta. As another example, a plurality of stents can be implanted upstream of the narrowing of the aorta. As another example, a plurality of stents can be implanted downstream of the narrowing of the aorta.

Results of Animal Study Using Radially Self-Expanding Stents

Figure 16B:
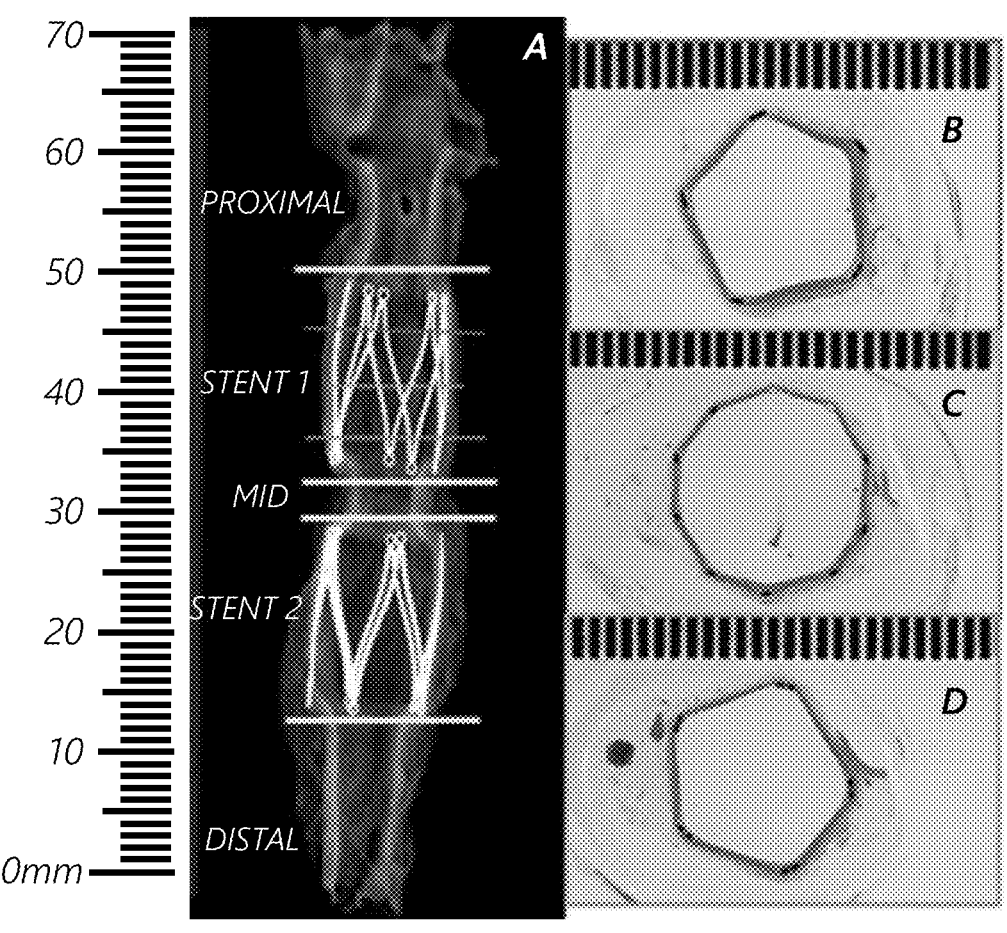
Figure 17:
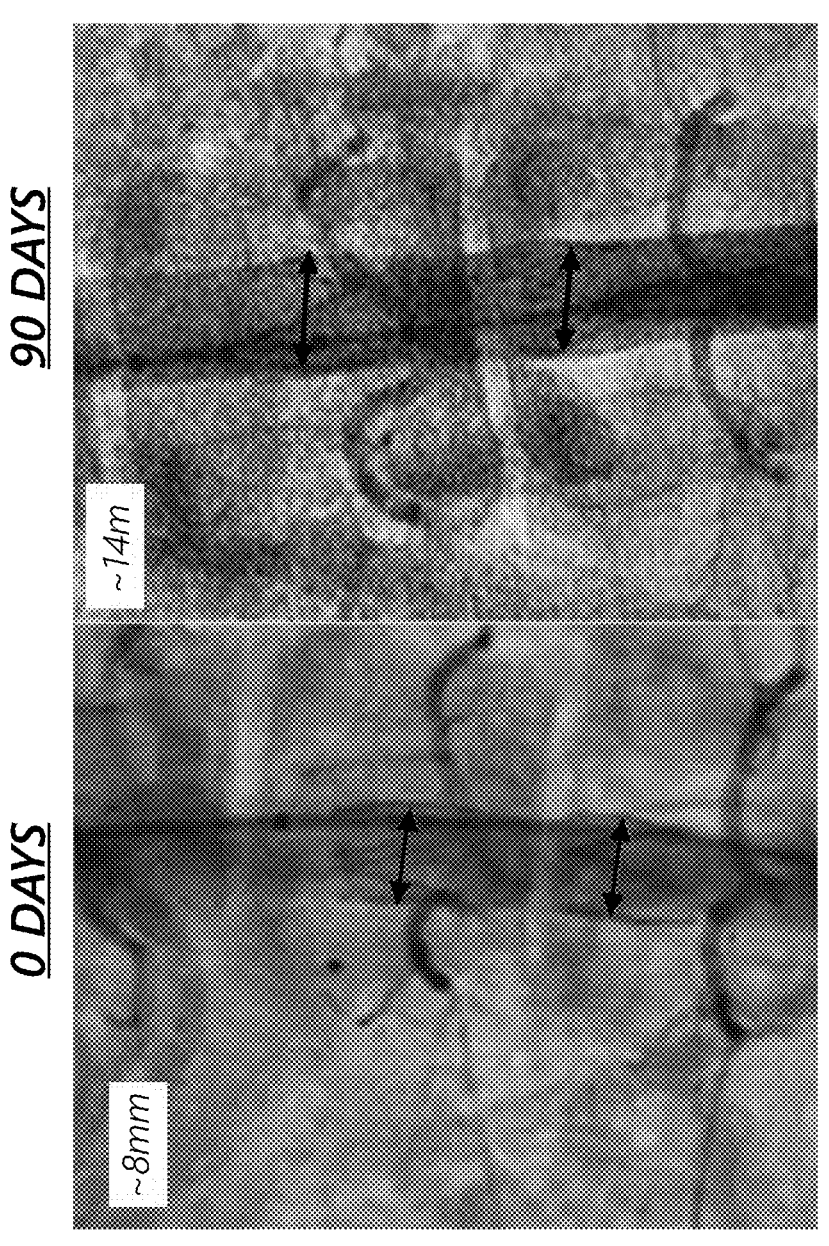
FIG. 17 illustrates an example of a radially self-expanding stent being used to expand an artery of an animal over the course of 90 days.

FIGS. 16A, 16B, and 17 illustrate an example of stents being implanted in an abdominal artery of an animal for 160 days. Prior to implantation of the stent, the artery diameter was about 8 mm. After 160 days, the artery diameter was about 14 mm. The stent expanded with expansion of the artery. No damage was observed to the vessels. For example, there were no signs of rupture, chronic damage, or aneurysm.

FIG. 16A illustrates two stents implanted in the artery. FIG. 16B illustrates the two stents on the left, one above the other with respect to how they are positioned on the page, and cross-sections of the top stent (Stent 1) at 3 locations. The cross-section labeled B corresponds to the most proximal cross-section indicated by the most-proximal line across Stent 1, the cross-section labeled D corresponds to the most distal cross-section indicated by the most-distal line across Stent 1, and the cross-section labeled C corresponds to the cross-section indicated by the line between the most-proximal line and the most-distal line. As shown in FIG. 16B, the inward pressure of the artery causes the stent to assume a peripheral shape that is not perfectly annular or circular and depends at least in part on the configuration of the struts and joints of the stent. The stents in FIGS. 16A and 16B are similar to the stent 200 described herein with reference to FIGS. 2A-2E.

FIG. 17 illustrates the two stents implanted in the artery at day 0, on the left, and the two implanted stents at day 160, on the right. In the image on the left, the diameter of the artery was about 8 mm. In the image on the right, the diameter of the artery had been increased due to the outward radial forces of the implanted stents to be about 14 mm after 160 days.

The hourglass-type shapes produced as shown in FIGS. 16A, 16B, and 17 demonstrate the relative growth/expansion of areas of a vessel associated with a radially self-expanding stent in accordance with embodiments of the present disclosure compared to the same vessel in an area without such a stent associated therewith. In the examples shown, the stents implanted show expansion/growth greater than that of the native vessel outside of the stent. For example, according to some measurements, the vessel expanded from approximately 8 to 14 mm post operatively where the stent was positioned compared to expansion from approximately 4 to 9 mm. Furthermore, substantially no necrosis or damage to the endothelial cells resulted. In addition, the respective stents dis not migrate out of the vessel or cause rupturing in the vessel. That is, the outward radial force of the stents was enough to open up the artery and grow, but not enough go damage the vessel.

Additional Embodiments and Terminology

While various embodiments have been described above, it should be understood that they have been presented by way of example only, and not limitation. Where schematics and/or embodiments described above indicate certain components arranged in certain orientations or positions, the arrangement of components may be modified. While the embodiments have been particularly shown and described, it will be understood that various changes in form and details may be made.

The present disclosure describes various features, no single one of which is solely responsible for the benefits described herein. It will be understood that various features described herein may be combined, modified, or omitted, as would be apparent to one of ordinary skill. Other combinations and sub-combinations than those specifically described herein will be apparent to one of ordinary skill, and are intended to form a part of this disclosure.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." The word "coupled", as generally used herein, refers to two or more elements that may be either directly connected, or connected by way of one or more intermediate elements. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or" in reference to a list of two or more items, that word covers all of the following interpretations of the word: any of the items in the list, all of the items in the list, and any combination of the items in the list.

The disclosure is not intended to be limited to the implementations shown herein. Various modifications to the implementations described in this disclosure may be readily apparent to those skilled in the art, and the generic principles defined herein may be applied to other implementations without departing from the spirit or scope of this disclosure. The teachings of the invention provided herein can be applied to other methods and systems and are not limited to the methods and systems described above, and elements and acts of the various embodiments described above can be combined to provide further embodiments. Accordingly, the novel methods and systems described herein may be embodied in a variety of other forms; furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure.

What is claimed is:

1. A method for treating aortic coarctation, the method comprising:

delivering a radially self-expanding stent in a crimped state;

deploying the radially self-expanding stent at a location of a narrowed vessel; and releasing the radially self-expanding stent such that the radially self-expanding stent produces a radially outward force that expands the narrowed vessel of a patient, wherein the radially outward force is at least 15 N when a diameter of the radially self-expanding stent is less than or equal to 2 mm.

2. The method of claim 1, wherein the patient is a human child that weighs less than or equal to 10 kg.

3. The method of claim 1, wherein a diameter of the radially self-expanding stent varies from a compact diameter to a fully expanded diameter.

4. The method of claim 3, wherein the compact diameter is less than or equal to 2 mm.

5. The method of claim 3, wherein the fully expanded diameter is at least 20 mm.

* * * * *